(12) United States Patent
Inoue

(10) Patent No.: US 7,158,661 B2
(45) Date of Patent: Jan. 2, 2007

(54) RADIOGRAPHIC IMAGE PROCESSING METHOD, RADIOGRAPHIC IMAGE PROCESSING APPARATUS, RADIOGRAPHIC IMAGE PROCESSING SYSTEM, PROGRAM, COMPUTER-READABLE STORAGE MEDIUM, IMAGE DIAGNOSIS ASSISTING METHOD, AND IMAGE DIAGNOSIS ASSISTING SYSTEM

(75) Inventor: Hitoshi Inoue, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 688 days.

(21) Appl. No.: 10/291,580

(22) Filed: Nov. 12, 2002

(65) Prior Publication Data

US 2003/0190064 A1 Oct. 9, 2003

(30) Foreign Application Priority Data

Apr. 3, 2002 (JP) .............................. 2002/101207
Apr. 3, 2002 (JP) .............................. 2002/101373
Aug. 26, 2002 (JP) .............................. 2002/245283

(51) Int. Cl.
*G06K 9/00* (2006.01)

(52) U.S. Cl. ..................................... 382/128

(58) Field of Classification Search ................ None
See application file for complete search history.

(56) References Cited

U.S. PATENT DOCUMENTS

| | | | | |
|---|---|---|---|---|
| 4,677,478 A | * | 6/1987 | Kruger et al. ........... 378/98.12 |
| 4,689,670 A | | 8/1987 | Okazaki ................... 358/111 |
| 4,939,757 A | * | 7/1990 | Nambu .......................... 378/8 |
| 5,090,042 A | * | 2/1992 | Bejjani et al. ............. 378/98.2 |
| 5,343,390 A | * | 8/1994 | Doi et al. ................... 382/132 |
| 5,359,513 A | * | 10/1994 | Kano et al. ................. 382/128 |
| 5,485,500 A | * | 1/1996 | Baba et al. ................. 378/98.2 |
| 5,807,256 A | * | 9/1998 | Taguchi et al. ............. 600/425 |
| 5,960,102 A | * | 9/1999 | Van Eeuwijk et al. ...... 382/128 |
| 5,982,915 A | * | 11/1999 | Doi et al. ................... 382/130 |
| 5,995,669 A | | 11/1999 | Shingu et al. .............. 382/237 |
| 6,219,405 B1 | | 4/2001 | Inoue ........................ 378/98.8 |
| 6,282,306 B1 | | 8/2001 | Inoue et al. ................. 382/132 |
| 6,504,892 B1 | * | 1/2003 | Ning .............................. 378/4 |
| 6,802,813 B1 | * | 10/2004 | Schutt ........................ 600/454 |
| 2002/0050986 A1 | * | 5/2002 | Inoue et al. ................ 345/204 |
| 2002/0097901 A1 | * | 7/2002 | Xu et al. .................... 382/131 |
| 2002/0151780 A1 | | 10/2002 | Klotz ......................... 600/407 |
| 2003/0095692 A1 | * | 5/2003 | Mundy et al. .............. 382/128 |
| 2005/0207630 A1 | * | 9/2005 | Chan et al. ................. 382/131 |

OTHER PUBLICATIONS

Katsuragawa, S., et al., "Possibility of Computer-Aided Diagnosis For Interstitial Diseases," Journal of Japanese Radiology Society, vol. 50, No. 7 (1990), pp. 753-766.
Sasaki, Y., et al., "Quantitative Evaluation of Pneumoconiosis Reference Radiographs With Texture Analysis," Journal of Japanese Radiology Society, vol. 52, No. 10 (1992), pp. 1385-1393.

* cited by examiner

*Primary Examiner*—Samir Ahmed
*Assistant Examiner*—O'Neal R. Mistry
(74) *Attorney, Agent, or Firm*—Fitzpatrick, Cella, Harper & Scinto

(57) ABSTRACT

This invention provides a radiographic image processing method of processing a group of radiographs including a moving-state radiographic image consisting of a plurality of radiographs representing a moving state of an object. The method includes specifying a region of interest for a plurality of radiographs included in the group of radiographs, and outputting diagnosis assisting information for assisting in diagnosis based on the group of radiographs, in accordance with the specified region of interest.

10 Claims, 27 Drawing Sheets

FIG. 8
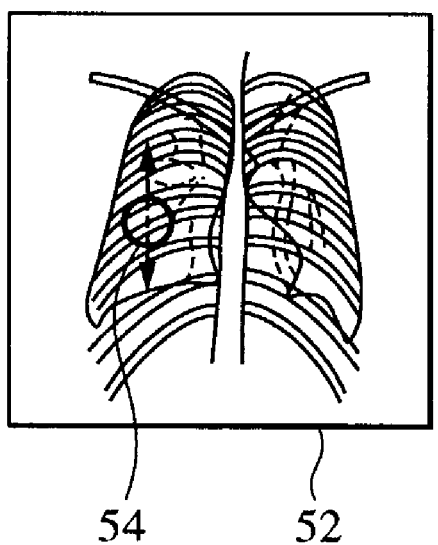
54   52
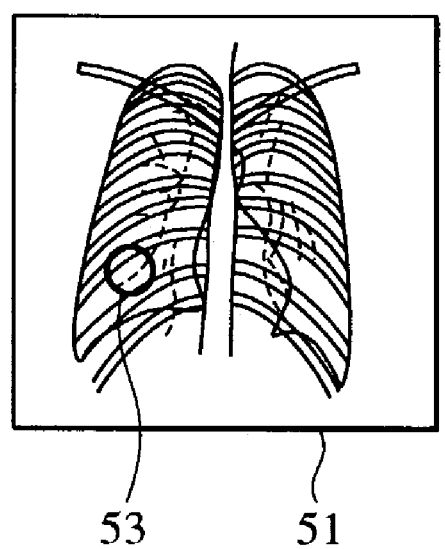
53   51

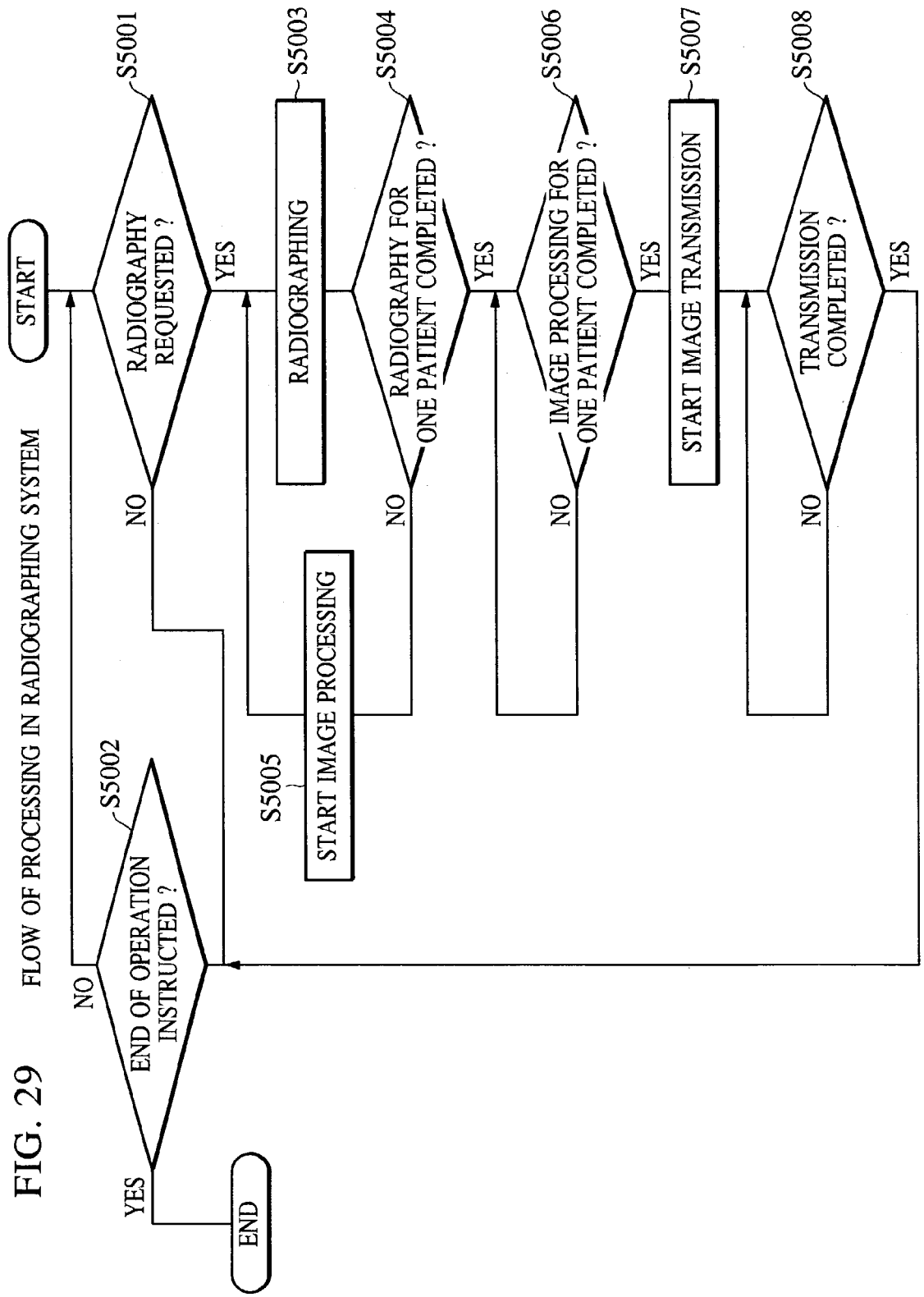
FIG. 29 FLOW OF PROCESSING IN RADIOGRAPHING SYSTEM

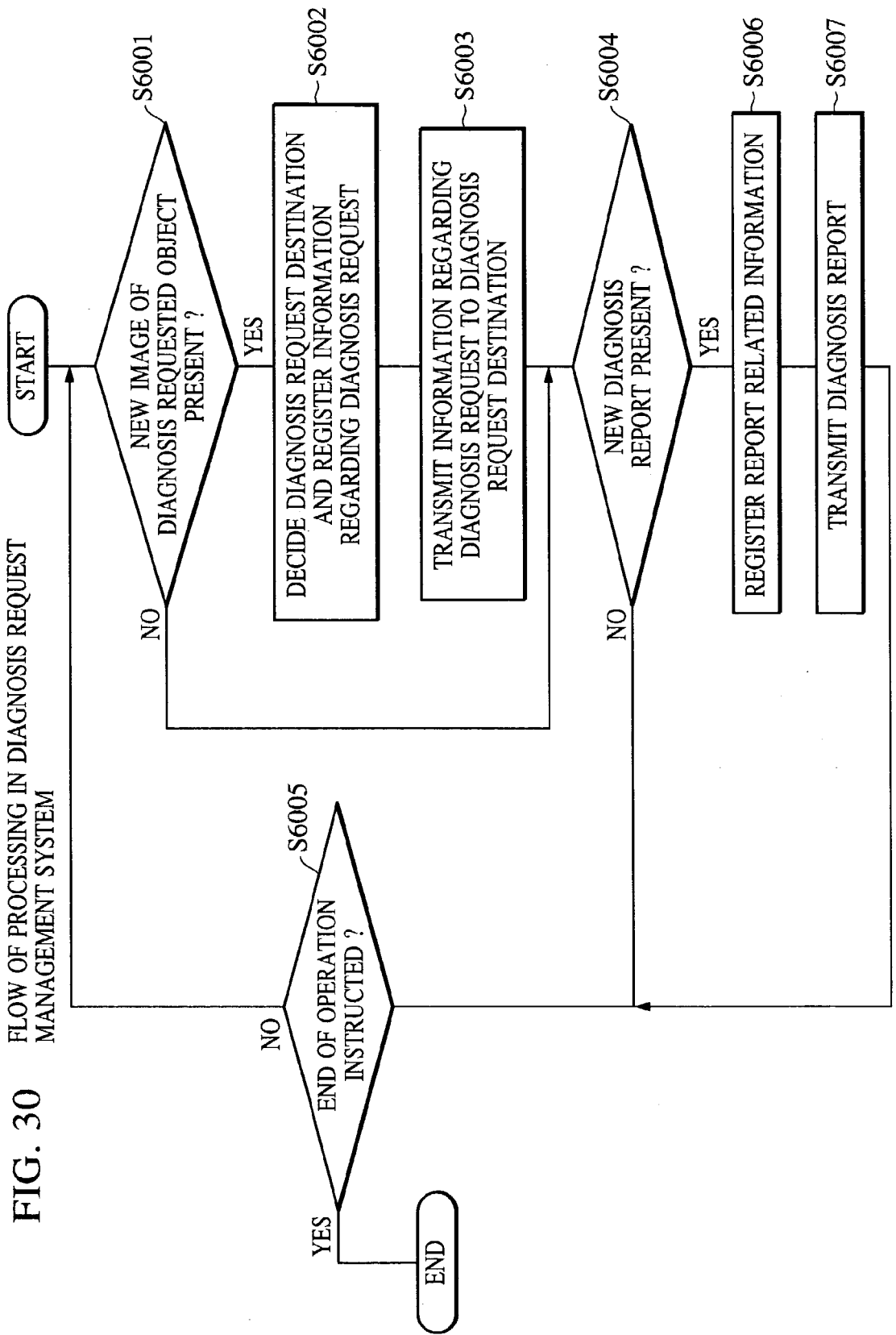

RADIOGRAPHIC IMAGE PROCESSING METHOD, RADIOGRAPHIC IMAGE PROCESSING APPARATUS, RADIOGRAPHIC IMAGE PROCESSING SYSTEM, PROGRAM, COMPUTER-READABLE STORAGE MEDIUM, IMAGE DIAGNOSIS ASSISTING METHOD, AND IMAGE DIAGNOSIS ASSISTING SYSTEM

BACKGROUND OF THE INVENTION

1. Field of the Invention

The present invention relates to a radiographic image processing method, a radiographic image processing apparatus, a radiographic image processing system, a program, a computer-readable storage medium, an image diagnosis assisting method, and an image diagnosis assisting system.

2. Description of the Related Art

Techniques for utilizing the ability of radiation such as X-rays to pass through many or most materials, and imaging a distribution of transmittance of the radiations have been the basis for development of a great deal of modern medical technology. Since the discovery of X-rays, a distribution of X-ray intensity has been imaged by a method of converting the distribution of X-ray intensity to visible light with a phosphor, forming a latent image on a silver-salt film with the visible light, and then developing the latent image. Recently, when obtaining an X-ray image in digital form, a method employing the so-called imaging plate has been popularized, in which a photostimulable phosphor is used to form a latent image representing a distribution of energy accumulated in the photostimulable phosphor upon irradiation by X-rays, and a laser beam illumination is used to excite the photostimulable phosphor to read the latent image, thus obtaining a digital image. Further, with the progress of semiconductor technology, a large-sized solid-state image pickup device capable of covering the size of a human body, i.e., the so-called flat panel detector, has been developed and has contributed to directly digitizing an X-ray image without forming a latent image, and thus to realizing more efficient diagnosis.

Meanwhile, with development of a highly-sensitive image pickup device utilizing an image intensifier, it has become possible to form an image of fluorescence generated with weak X-rays and to observe a moving state of the interior of a human body. This method has also been put into general use. Then, the latest flat panel detector has sensitivity comparable that of the image pickup device utilizing an image intensifier, and has become applicable to radiographing a moving state of even a large region or portion of a human body.

The most effective radiography in medical use is radiography of the chest of the human body. Radiographing of a wide region, including the chest, but covering the abdomen as well, is useful for discovering many diseases, including lung diseases, and therefore radiographing of the chest is essential in standard health examination, e.g., a general physical examination. Also, in order efficiently to diagnose a large amount of X-ray chest images radiographed for health examination, so-called Computer-Aided Diagnosis (CAD) has been recently put into practice, in which digital X-ray chest images are analyzed using a computer so as to assist doctors in initial diagnosis.

In diagnosis, it is effective to obtain a moving-state image of the chest, which represents a moving state due to breathing, etc., using the above-mentioned large-sized flat panel detector and to observe the moving state.

However, diagnosis based on a still image (film) representing the maximum inhalation state of chest is a reliable diagnosis method that has been practiced for many years, and doctors are well experienced in the diagnosis based on the still image. Conversely, it is probably thought that, in not a few cases, doctors cannot sufficiently recognize information useful for diagnosis that could be obtained from observing a moving-state image of the chest. Further, because the moving-state image is generally radiographed with a small dose, reliability of detailed image information obtained in this fashion is relatively low. Hence, diagnosis information based on the conventional still images remains very important.

In addition, conventional CAD for a general radiograph of the chest has been usually performed on one radiographed image. This is attributable to the fact that there has been only a generally radiographed still image as an image for use in initial diagnosis. Consequently, the amount of information available in CAD is small, which has been one factor causing a stagnation in detection accuracy of the CAD.

SUMMARY OF THE INVENTION

Accordingly, it is an object of the present invention to overcome the above-mentioned problems in the related art.

According to the present invention, the foregoing object is attained by providing a radiographic image processing method of processing a group of radiographs including a moving-state radiographic image consisting of a plurality of radiographs representing a moving state of an object, comprising a region specifying step, of specifying a region of interest for a plurality of radiographs included in the group of radiographs; and an outputting step, of outputting diagnosis assisting information for assisting diagnosis based on the group of radiographs in accordance with the region of interest specified in the region specifying step.

According to the present invention, the foregoing object is also attained by providing a radiographic image processing apparatus for processing a group of radiographs including a moving-state radiographic image consisting of a plurality of radiographs representing a moving state of an object, comprising a region specifying unit for specifying a region of interest for a plurality of radiographs included in the group of radiographs; and an outputting unit for outputting diagnosis assisting information for assisting diagnosis based on the group of radiographs in accordance with the region of interest specified using the region specifying unit.

Further, the foregoing object is also attained by providing a radiographic image processing system, including a plurality of apparatuses, for processing a group of radiographs including a moving-state radiographic image consisting of a plurality of radiographs representing a moving state of an object, comprising a region specifying unit for specifying a region of interest for a plurality of radiographs included in the group of radiographs; and an outputting unit for outputting diagnosis assisting information for assisting diagnosis based on the group of radiographs in accordance with the region of interest specified by the region specifying unit.

Further, the foregoing object is also attained by providing a program for causing a computer to execute a radiographic image processing method of processing a group of radiographs including a moving-state radiographic image consisting of a plurality of radiographs representing a moving state of an object, the method comprising a region specifying step, of specifying a region of interest for a plurality of radiographs included in the group of radiographs; and an outputting step, of outputting diagnosis assisting information for assisting diagnosis based on the group of radiographs in accordance with the region of interest specified in the region specifying step.

Further, the foregoing object is also attained by providing a computer-readable storage medium storing a program for causing a computer to execute a radiographic image processing method of processing a group of radiographs including a moving-state radiographic image consisting of a plurality of radiographs representing a moving state of an object, the method comprising a region specifying step, of specifying a region of interest for a plurality of radiographs included in the group of radiographs; and an outputting step, of outputting diagnosis assisting information for assisting diagnosis based on the group of radiographs in accordance with the region of interest specified in the region specifying step.

Furthermore, the foregoing object is also attained by providing an image diagnosis assisting method of assisting image diagnosis of an object, comprising a region specifying step, of specifying a region of interest for a plurality of radiographs included in a group of radiographs, which includes a moving-state radiographic image consisting of radiographs representing a moving state of an object; an outputting step, of outputting diagnosis assisting information for assisting diagnosis based on the group of radiographs in accordance with the region of interest specified in the region specifying step; a storing step, of storing the diagnosis assisting information output in the outputting step in association with the group of radiographs; and a transmitting step, of transmitting the group of radiographs stored in the storing step to a remote computer via a LAN and/or a WAN.

Furthermore, the foregoing object is also attained by providing an image diagnosis assisting system for assisting image diagnosis of an object, comprising a region specifying unit for specifying a region of interest for a plurality of radiographs included in a group of radiographs, which includes a moving-state radiographic image consisting of radiographs representing a moving state of an object; an outputting unit for outputting diagnosis assisting information for assisting diagnosis based on the group of radiographs in accordance with the region of interest specified by the region specifying unit; a storing unit for storing the diagnosis assisting information output by the outputting unit in association with the group of radiographs; and a transmitting unit for transmitting the group of radiographs stored by the storing unit to a remote computer via a LAN and/or a WAN.

Further objects, features and advantages of the present invention will be apparent from the following descriptions of the preferred embodiments taken in conjunction with reference to the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 8 schematically shows a manner of marking corresponding regions.

FIG. 29 is a flowchart for explaining a flow of processing of a radiographing system.

FIG. 30 is a flowchart for explaining a flow of processing of a diagnosis request management system.

DESCRIPTION OF THE PREFERRED EMBODIMENTS

Preferred embodiments of the present invention will be described in detail in accordance with the accompanying drawings.

(First Embodiment)

Figure 4:
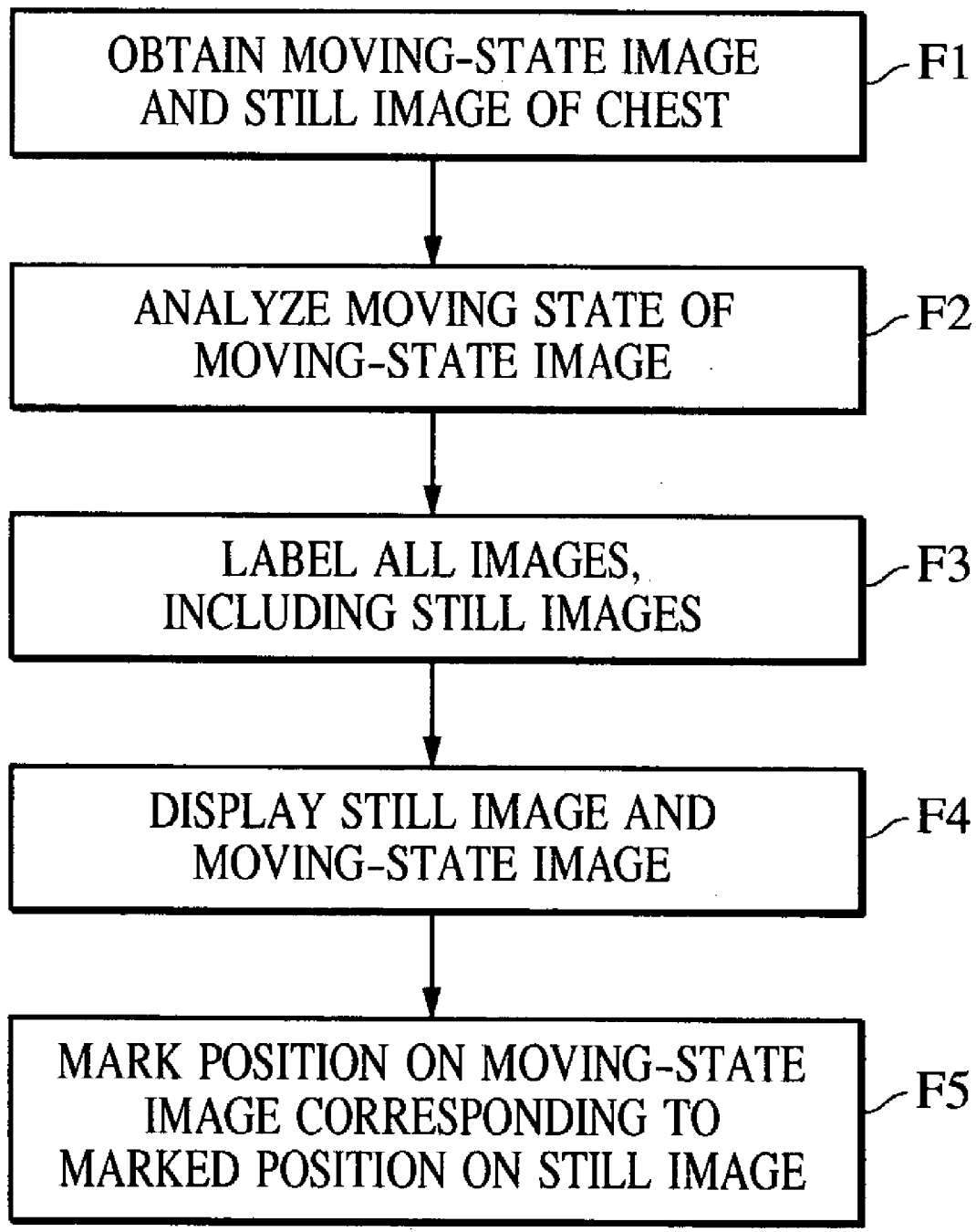
FIG. 4 is a flowchart of the first embodiment.

This first embodiment includes the operations of steps F1 to F5 shown in a flowchart of FIG. 4. The operations of the steps F1 to F5 are described below in the order named.

First, a description is made of the step F1 of "obtaining a moving state image and a still image of the chest".

Figure 1:
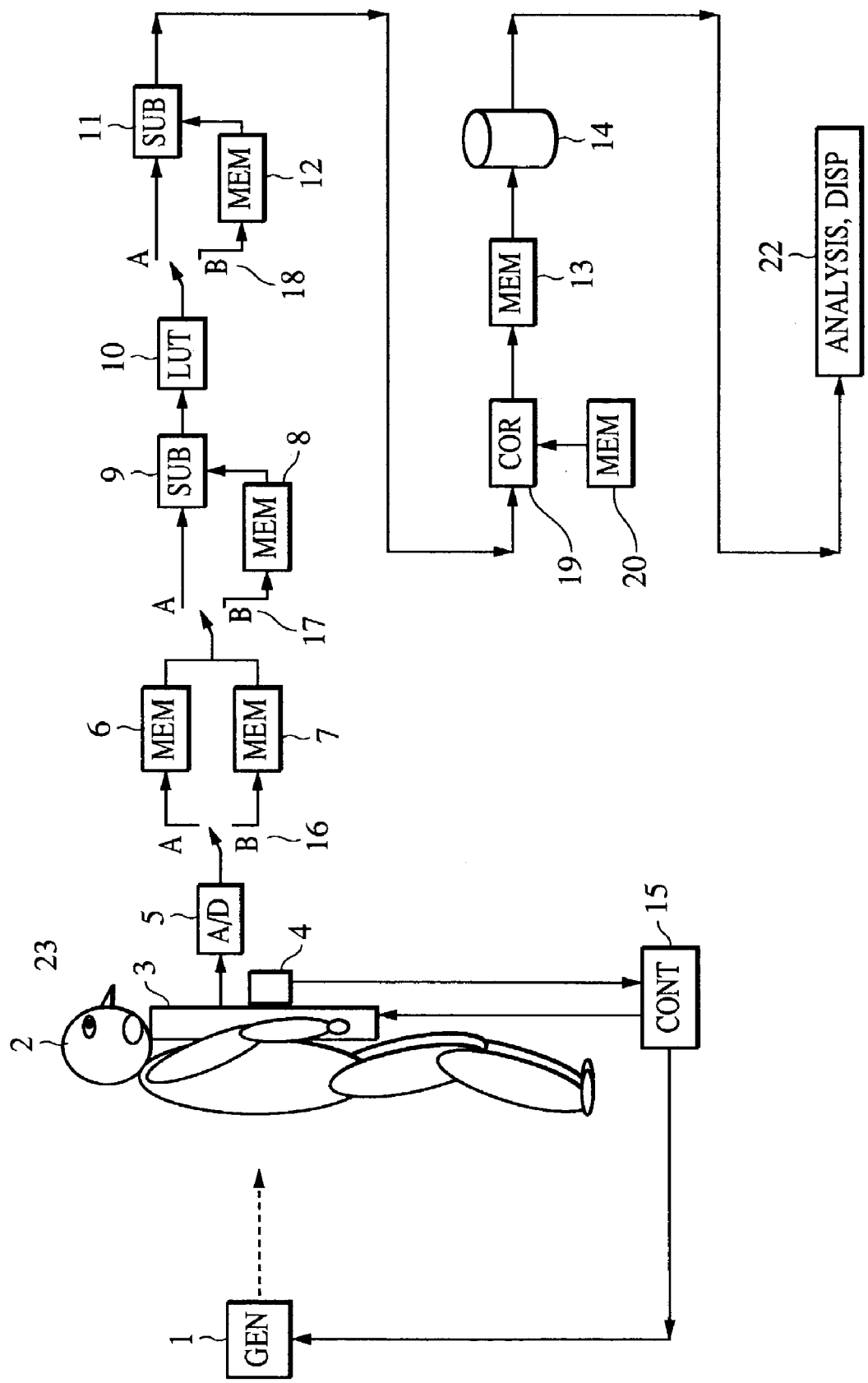
FIG. 1 is a block diagram schematically showing a first embodiment of the present invention.

FIG. 1 is a block diagram schematically showing the first embodiment of the present invention. An X-ray generator (X-ray source) 1 radiates X-rays in the direction the dotted-line arrow as shown. In this case, for radiographing the chest of a human body (patient) 2, i.e., a subject (also sometimes preferred to as the "object"), the X-rays enter the human body from the back side, and a radiographic image of the chest is obtained. A flat panel detector 3 for imaging a distribution of the X-ray intensity includes a plurality of image receiving devices (referred to simply as "pixels"), which are arrayed on an image receiving surface in a matrix pattern and correspond to a plurality of pixels constituting an image. The pixels in the matrix pattern are usually arrayed at equal intervals of 100 μm to 200 μm pitch.

A so-called photo-timer 4 monitors the amount of X-rays having passed through the human body, for effecting control such that the amount of X-rays to which the human body is exposed, is optimum. Each pixel value output from the flat panel detector 3 is an analog voltage signal in an initial stage, and hence it is converted to a digital value, i.e., a numerical value, by an A/D converter 5. Usually, at least the A/D converter 5 is disposed in the same housing as is the flat panel detector 3. Looking from the outside, therefore, it appears as if a digital value (image data) were directly output from the flat panel detector 3. Buffer memories 6, 7 store temporarily image data and serve as a so-called double buffer. While one of the buffer memories 6, 7 is reading in image data, the other is reading out image data. A switch 16 is used so as to maintain continuity of the reading-out process.

A subtractor 9 has the function of subtracting image data (offset image), which has been obtained from the detector while the latter is not being irradiated with X-rays and stored in a memory 8 beforehand, from an actual image of the subject. More specifically, image data obtained from the detector when not receiving X-rays is stored in the memory 8 with a switch 17 turned to side B (see FIG. 1). Then, the switch 17 is turned to side A in actual use.

A lookup table 10 has the function of converting values of the image data. More specifically, the lookup table 10 is set so as to convert an input value to a value proportional to the logarithm of the input value. A subtractor 11 has the function of compensating a variation in gain for each pixel of the flat panel detector 3 by subtracting image data, which has been obtained by irradiating the detector with X-rays without a subject in place and converting the image data from the detector to logarithmic values, stored in a memory 12 beforehand, from an actual image of the subject. More specifically, X-rays are radiated in the absence of a subject to store image data representing variations in gain in the memory 12 with the switch 17 turned to side A and a switch 18 turned to side B. Then, when actually taking an image of the subject, the switches 17, 18 are both turned to side A.

A circuit shown as block 19 has the function of correcting defective pixels. Information regarding defective pixels of the flat panel detector 3 used in the actual system is stored in a memory 20 beforehand, and the block 19 estimates data of those defective pixels based on the data of surrounding normal pixels, thereby correcting the defective pixels. Generally, an average one of the data values of the surrounding normal pixels is used for that correction. The image having been thus subjected to the various corrections is temporarily stored in an image memory 13 and then recorded in a filing device 14.

The image data obtained as described above is sent to an analysis and display block 22. The image data is also sent to an external storage, display, image processor, etc., (not shown) for medical diagnosis. A block 15 represents a controller (control mechanism) for control of radiography. The controller 15 drives the flat panel detector 3 at the predetermined timing and outputs a trigger of an X-ray pulse to the X-ray generator 1 at the timing of radiation.

Figure 2:
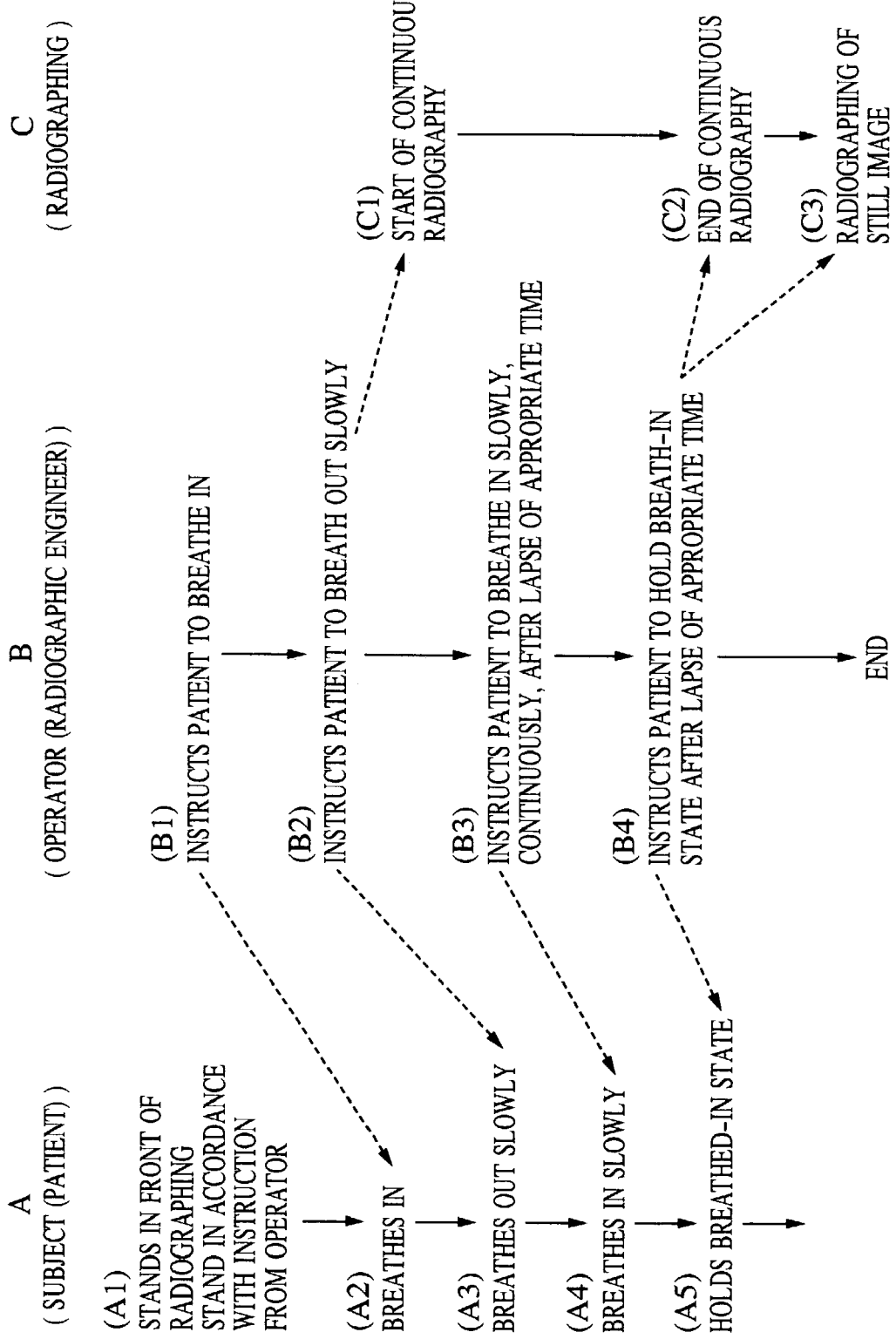
FIG. 2 is a chart representing one example of a radiography sequence.

FIG. 2 shows a radiography sequence. The left-hand column A represents actions of the patient (the subject), the central column B represents actions of a radiographic engineer as an operator, and the right-hand column C represents a mode of a radiographing apparatus. At the first timing (A1), the patient stands in front of a radiographing stand (as denoted by 2 in FIG. 1) in accordance with an instruction from the operator. At the next timing (B1), the operator instructs the patient to breathe in, and then instructs to breathe out slowly, from the timing (B2). In accordance with those instructions, the patient breathes in (A2), and then breathes out slowly (A3). In parallel, the operator operates the radiographing apparatus shown in FIG. 1 to start continuous radiography of the moving state of the patient's chest in breathing (C1). An interval of the radiographing is about 3 to 10 image frames per second. After the lapse of an appropriate time (several seconds) while looking at the situation of the patient, the operator now instructs the patient to breathe in slowly (B3). At this timing, the continuous radiography is still continued. While looking at the situation of the patient, when the patient has breathed in to the full, the operator instructs the patient to hold the breath in (B4). At this timing, collection of continuous image data representing the moving state in breathing is brought to an end (C2). Then, the state in which the patient holds the breath is radiographed as a still image (C3).

Figure 3:
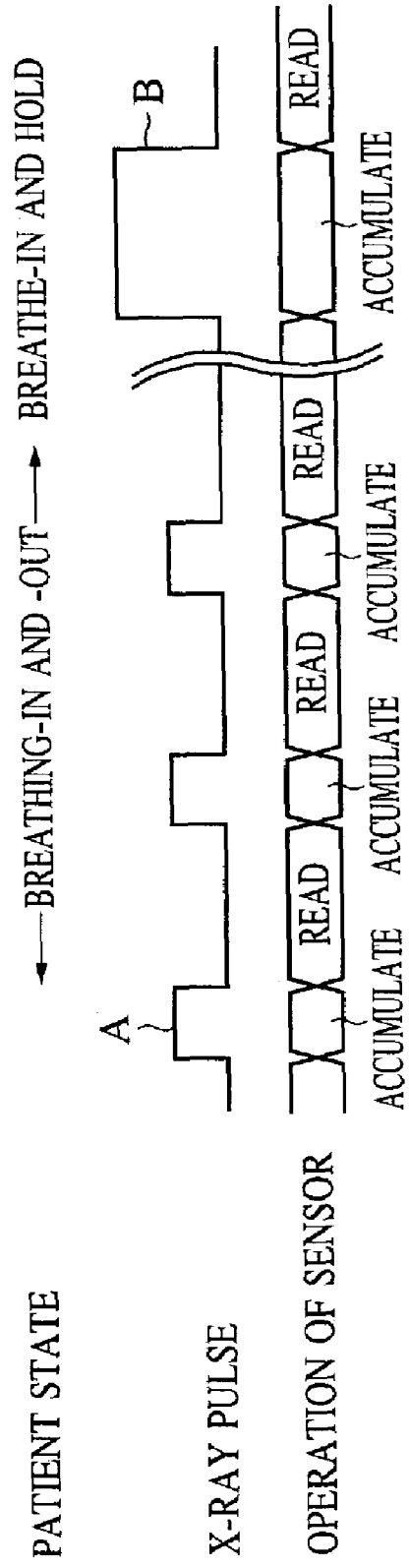
FIG. 3 is a timing chart for the radiography sequence.

FIG. 3 is a timing chart schematically showing the radiography sequence. The upper row represents the patient's state, the middle row represents an X-ray pulse, and the lower row represents the operation of a sensor system including the flat panel detector 3. At the timing at which the patient breathes in or out in accordance with the instruction from the operator, an X-ray pulse with a magnitude A is issued. During a period in which the X-ray pulse is being issued, the sensor system accumulates image information, and during the remaining period, it reads the accumulated image information. Then, at the timing B4, at which the patient holds the breath in, an X-ray pulse with a magnitude B, larger than A, is issued, and the sensor system reads image information because of the necessity of obtaining a stable and highly-quality image comparable to that obtainable with the conventional technique. At the timing B4, it is also possible to take a radiograph using the photo-timer 4 in FIG. 1. In such a case, when a total amount (integrated value) of X-rays measured by the photo-timer 4 reaches a predetermined value, the controller 15 sends an X-ray radiation stop signal to the X-ray generator 1, thereby stopping the X-ray radiation.

The photo-timer 4 can be used in radiography of not only the still image, but also for each frame of the moving-state image in breathing. In such a case, the photo-timer 4 is set to output a stop signal upon reaching a relatively small accumulative amount of X-rays when taking the moving state image, and to output a stop signal upon reaching a relatively large cumulative amount of X-rays when taking the still image.

With the above-described operations, the moving-state image in breathing and the still image can both be obtained while the patient is instructed to perform actions that are not much different from the action required in conventional health diagnosis, i.e., just slow deep breathing.

The order and the number of times of breathing in and out are not limited to those described above as the first embodiment. Also, the timing of taking the still image is not limited to the last in the sequence, but may be changed to a point in time immediately before the first breathing-in (or to any other desired point in time as the occasion requires). Further, the amount of X-rays is not always required to be increased in particular when taking the still image. In some cases, the relatively small amount of X-rays used for performing radiography of the moving-state image is also sufficient for performing radiography of the still image.

The analysis and display block 22 is a functional block of analyzing the obtained moving state image and still image. The analysis and display block 22 includes a display unit and is primarily made up of a program and a computer system. The operation described below is primarily executed in the analysis and display block 22. Additionally, the analysis and display block 22 may be constituted as an external unit independent of the radiographing apparatus.

The step F2, "analyze moving state of moving-state image", in FIG. 4, will be described below.

Figure 5:
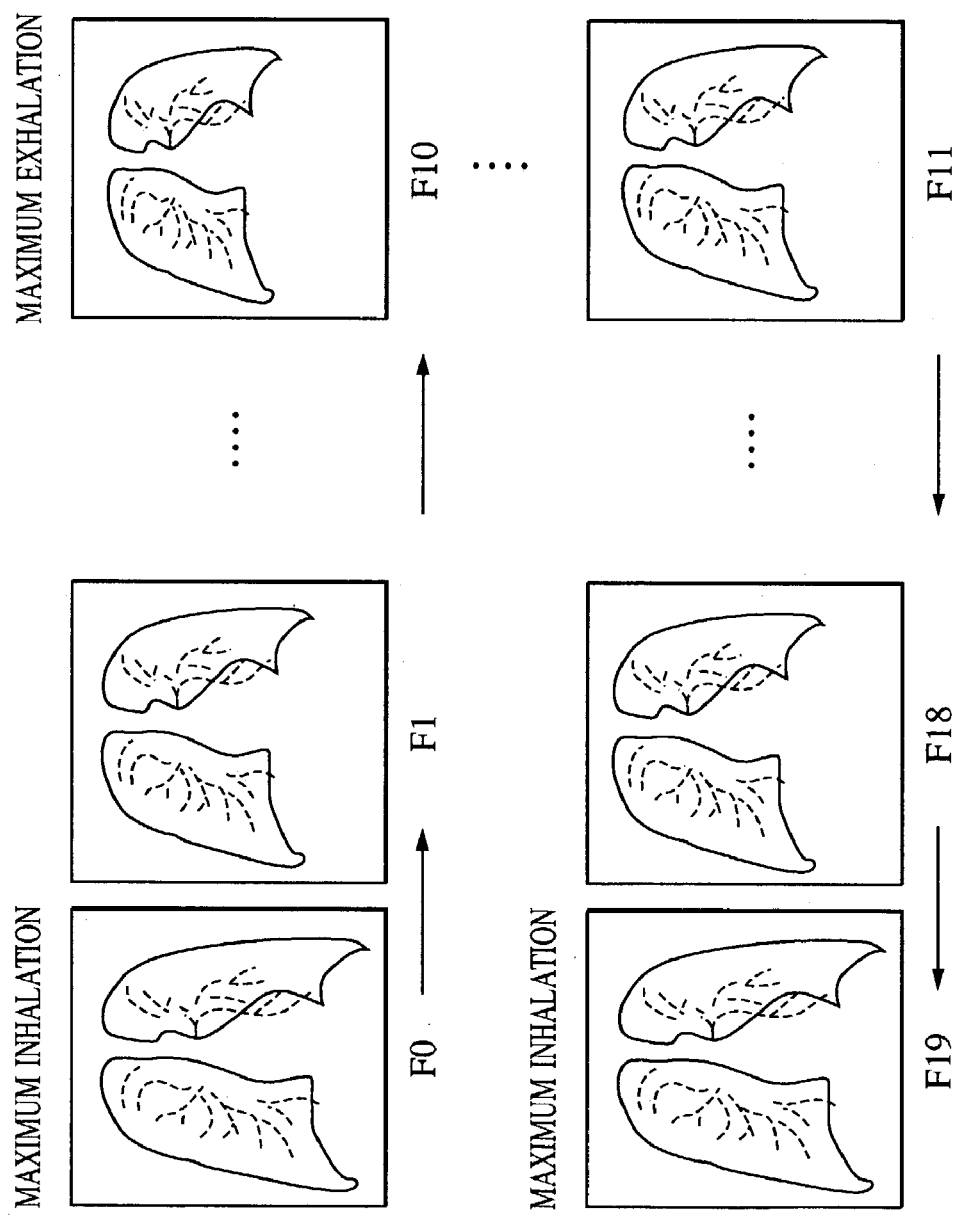
FIG. 5 schematically shows frames of a moving state image in breathing.

FIG. 5 schematically shows, by way of example, an image group consisting of 20 image frames representing respective moving states obtained during a period in which the patient lets out breath from the maximum inhalation state, and after reaching the maximum exhalation state, returns to the maximum inhalation state. In each of the image frames shown in FIG. 5, only the lung field is represented, and the contour, bones, etc., of the human body are omitted. Those image frames are obtained by imaging the expanded and contracted states of the same location (lung field) of the same person. Since the same anatomical portion can be regarded as moving with breathing, it is possible to correlate images of the same anatomical portion with each other among the respective frames.

One conceivable method of correlating images of the same anatomical portion with each other comprises the steps of calculating motion vectors between successive image frames and determining which pixel of one image frame corresponds to which pixel of the other image frame. The motion vector can be determined by calculating a velocity vector at each portion, i.e., the so-called optical flow. The so-called gradient process and block matching process are known as methods for calculating the optical flow.

The step F3 of "labeling all of the images frames including the still image" in FIG. 4 will be described below.

Figure 6:
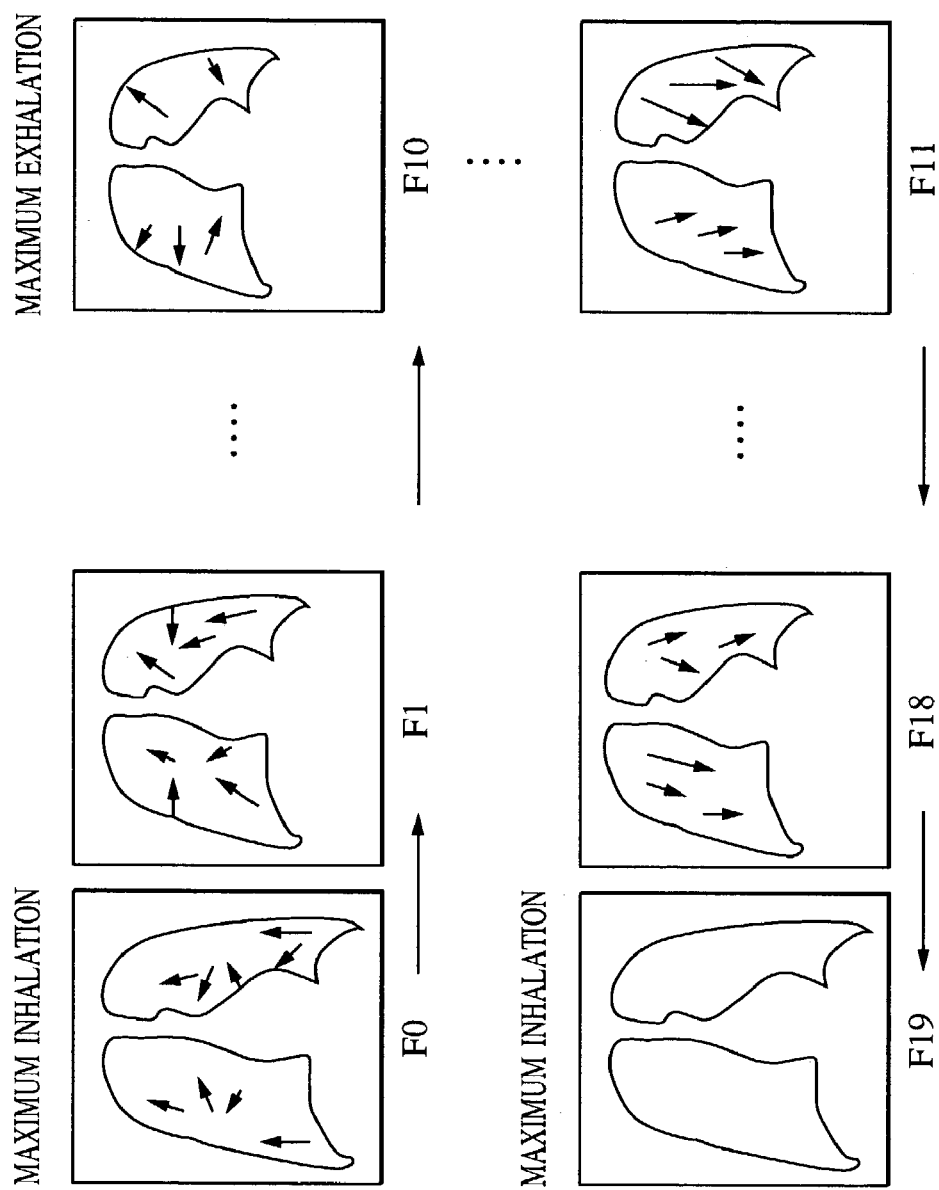
FIG. 6 schematically shows a set of results of calculating motion vectors between successive two frames of the moving state image in breathing.

FIG. 6 schematically shows a set of results of calculating motion vectors for each image frame with respect to an image frame of next phase. The motion vectors are calculated using a calculation block constituted by a group of adjacent pixels, and can be calculated on the pixel-by-pixel basis.

Figure 7:
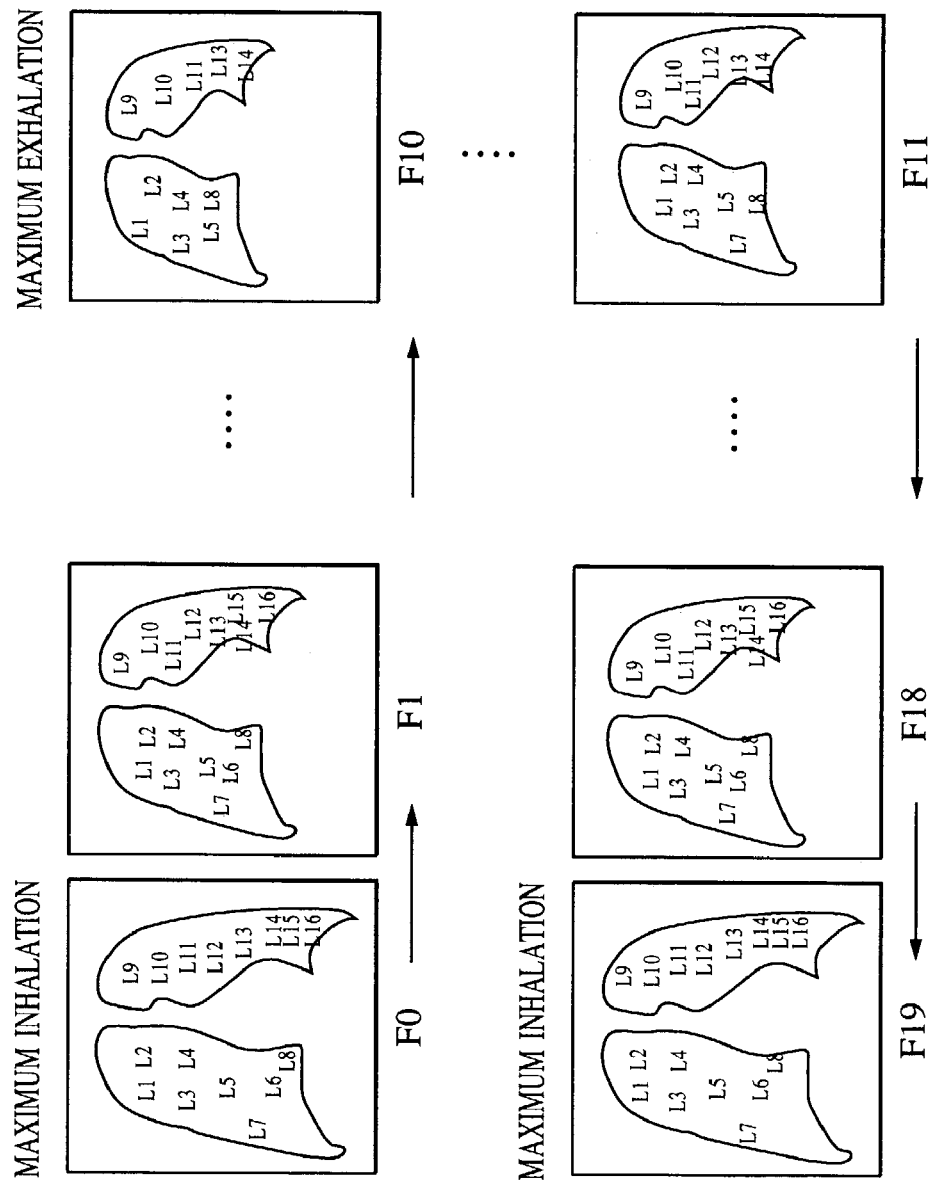
FIG. 7 schematically shows a set of results of labeling the frames of the moving state image in breathing.

Based on the calculation results of the motion vectors, it is possible to estimate at which position in another image the pixel (region) labeled on one image locates. FIG. 7 schematically shows results of labeling the image frames. In an initial stage of the calculation corresponding to the maximum inhalation state, in which the image has a maximum area and represents the largest number of locations, it is assumed to label pixel groups L1 to L16. These pixel groups are each a set of plural pixels, but labeling may be made for each pixel to form a larger number of labels. FIG. 7 represents how L1 to L16 move depending on the motion vectors. In the maximum exhalation state, in which the image has a minimum area, several pixel groups (regions) are overlapped with each other and the number of labels is reduced, while the corresponding locations are labeled. Also, since a still image corresponds to a frame of moving-state image F0, taken in the maximum inhalation state, the still image is labeled similarly to F0. With such labeling, corresponding locations (regions) in all of the image frames are correlated to each other.

The step F4 of "displaying the still image and the moving state image" in FIG. 4 will be described below.

FIG. 8 shows an example in which the still image and the moving state image thus obtained are displayed on the display unit in the analysis and display block 22. In FIG. 8, numeral 51 denotes the still image, and 52 denotes the moving-state image. The moving-state image is basically displayed including a series of motions. As shown in FIG. 8, both the still image and the moving-state image are preferably displayed side by side in a comparable manner. However, both images may be displayed using a plurality of separate display units, or they may be displayed side by side on one display screen divided into two areas. Depending on cases, the object of the present invention can also be achieved with a method of selectively displaying the two images in a switching manner.

The step F5 of "marking a position on the moving state image corresponding to the marked position on the still image" in FIG. 4 will be described below.

When the doctor recognizes on the still image 51 of FIG. 8 that there is a location suspicious for any disease, the doctor looks at the corresponding location on the moving-state image for carrying out diagnosis with high certainty. In this case, to specify the location (also referred to as the "region of interest") recognized on the still image, a mark is put on the still image as indicated by 53, for example. That marking is executed with computer programming. More specifically, the doctor designates the mark position 53 by employing a user interface, such as a mouse, whereupon a computer reads the designated position and marks the position 53 on the display unit.

Thereafter, the computer programming extracts the label at the position 53 in accordance with the above-described labeling, and marks the position of the same label on each frame of moving state image to display a mark. As a result of the above-described operation, the disease suspicious location (also referred to as the "region of interest") recognized by the doctor is marked on each moving-state image 52, and a manner in which the marked location moves with breathing is displayed.

By viewing the moving-state image thus marked, the doctor can observe and diagnose while focusing attention onto moving state of the disease-suspicious location.

Additionally, the computer programming may be set such that, when the disease-suspicious location is recognized on the moving-state image in the step F5, a corresponding position on the still image 51 is also marked upon marking of the moving-state image 52 to specify the recognized location with the user interface.

(Second Embodiment)

This second embodiment differs from the first embodiment in further comprising an image analysis (CAD, or Computer-Aided Diagnosis) step of detecting the disease-suspicious location by means of a computer.

Figure 9:
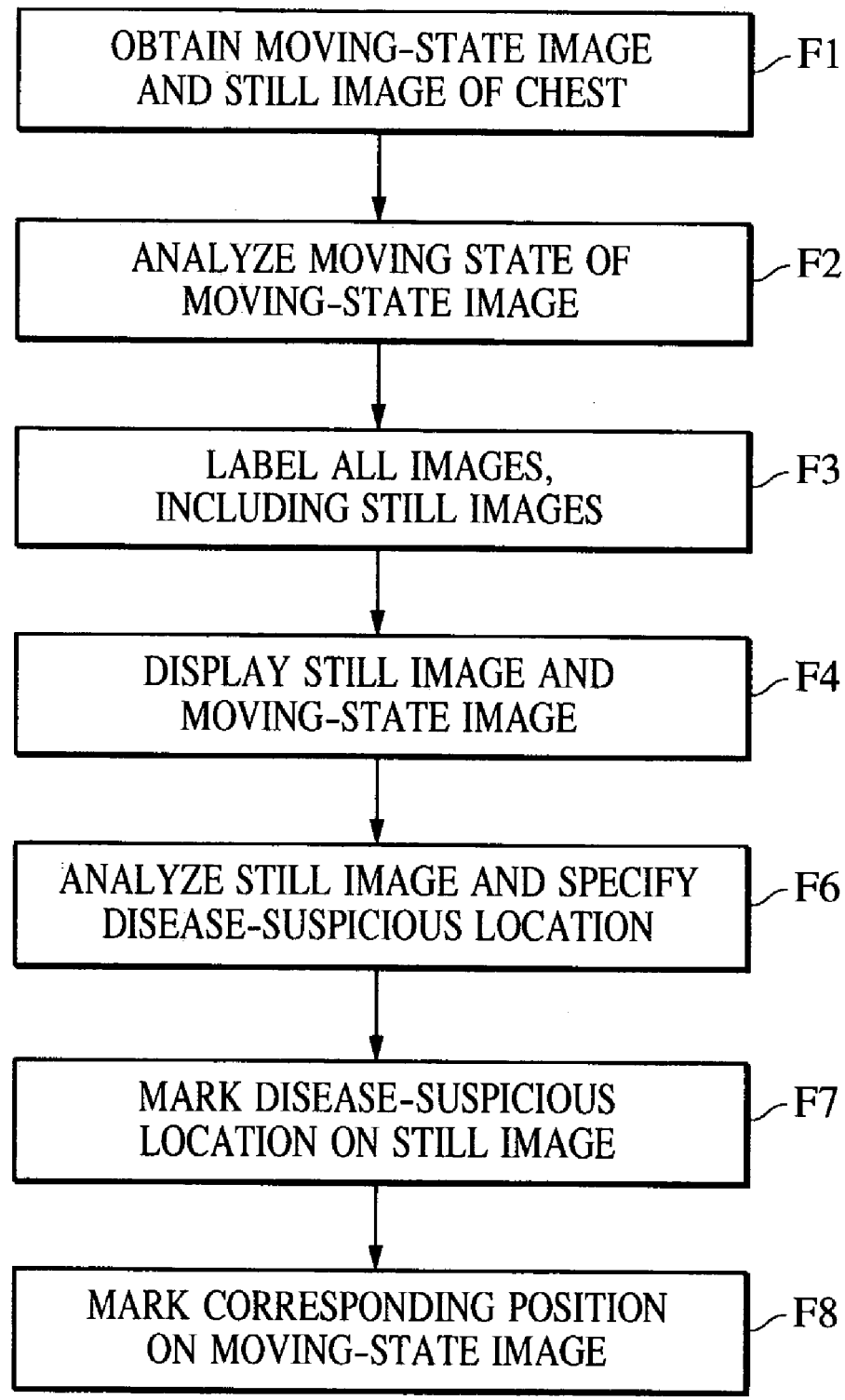
FIG. 9 is a flowchart of a second embodiment.

FIG. 9 is a flowchart showing the processing executed in this second embodiment. A description of steps F1 to F4, which are the same as those in FIG. 4, is omitted here.

In step F6, the still image is analyzed to specify the disease-suspicious location (referred to also as the "region of interest"). Some examples of the image processing in this step are stated in detail in papers given below:

Shigehiko Katsuragawa, et al., "Possibility of Computer-Aided Diagnosis for Interstitial Diseases", *Journal of Japan Radiological Society*, 50: 753–766, 1990; and Yasuo Sasaki, et al., "Quantitative Evaluation of Pneumoconiosis Reference Radiographs with Texture Analysis", *Journal of Japan Radiological Society*, 52: 1385–1393, 1992. The disclosures of these papers are incorporated herein by reference, in their entirety.

In step F7, marking is made at the disease-suspicious location detected in the step F6 similarly to the mark 53 shown in FIG. 8. Stated otherwise, while the doctor specifies the location in the first embodiment, the computer automatically carries out the marking in this second embodiment.

In step F8, a moving mark 54 is put on the corresponding location (referred to also as the "region of interest") in the moving state image 52 shown in FIG. 8. In such a manner, the diagnosis doctor is able to observe both the still image and the moving-state image and to make a diagnosis with high certainty while referring to the result of image analysis executed by the computer.

(Third Embodiment)

Figure 10:
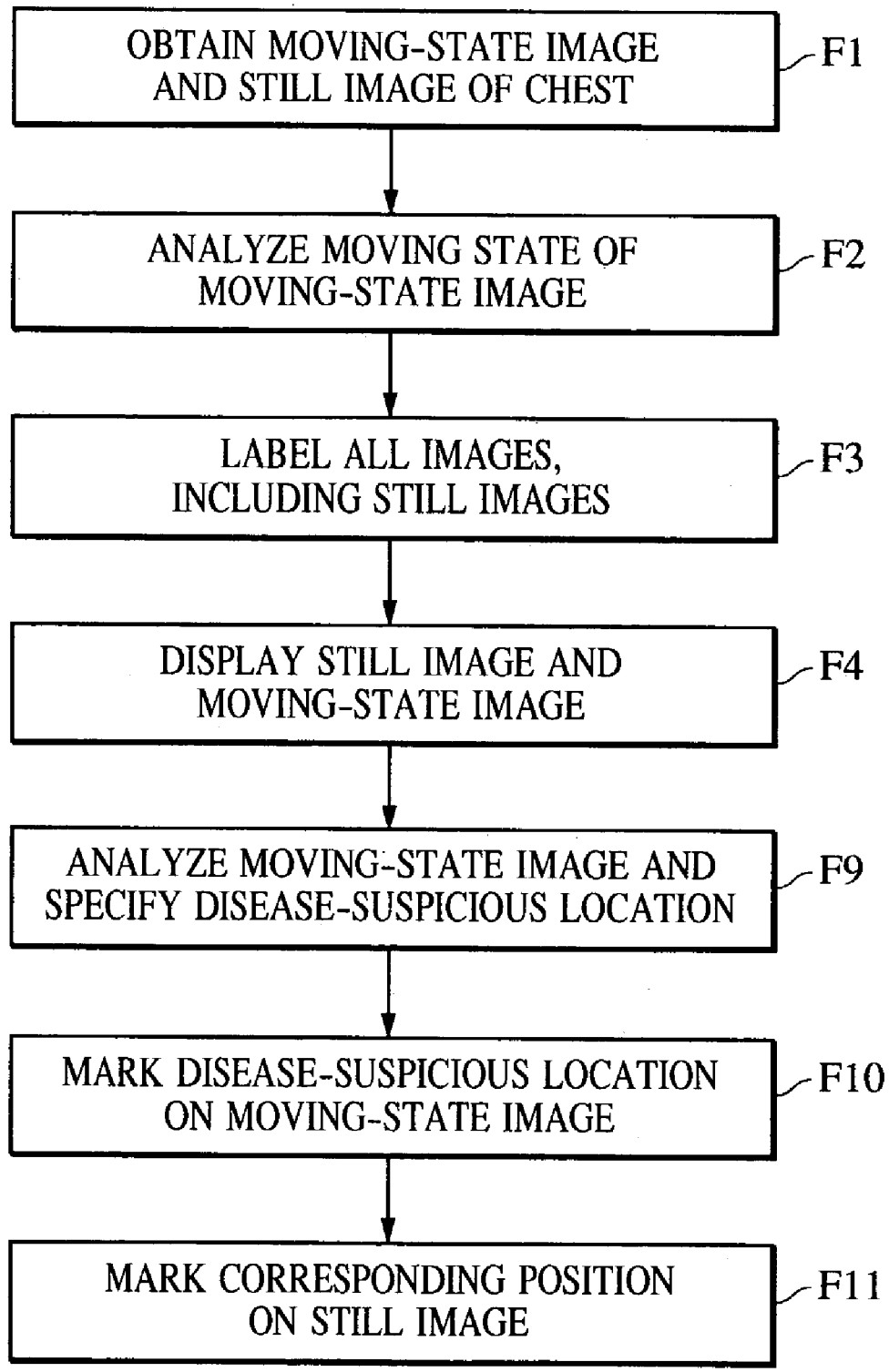
FIG. 10 is a flowchart of a third embodiment.

FIG. 10 is a flowchart showing the processing executed in this third embodiment. A description of the steps F1 to F4, which are the same as those in FIG. 4, is omitted here. In next step F9, the moving-state image is analyzed. With the analysis of the moving-state image, the disease-suspicious (disease-candidate) location (referred to also as the "region of interest") can be detected through computer-aided image analysis based on changes in motion vectors, in density at a particular part and in area size at each part.

In step F10, a moving mark is put on the moving-state image at the location detected in the step F9.

Then, in step F11, marking is made on the corresponding location (referred to also as the "region of interest") in the still image. As a result, the diagnosis doctor is able to observe both the still image and the moving-state image and to make a diagnosis with high certainty while referring to the result of image analysis executed by the computer.

While the first to third embodiments can be practiced independently of one another, it is also possible to combine at least two of the operations of those embodiments with each other.

(Fourth Embodiment)

This fourth embodiment differs from the first to third embodiments in its manner of displaying the moving-state image. The following description is made only of this point of difference.

Figure 11:
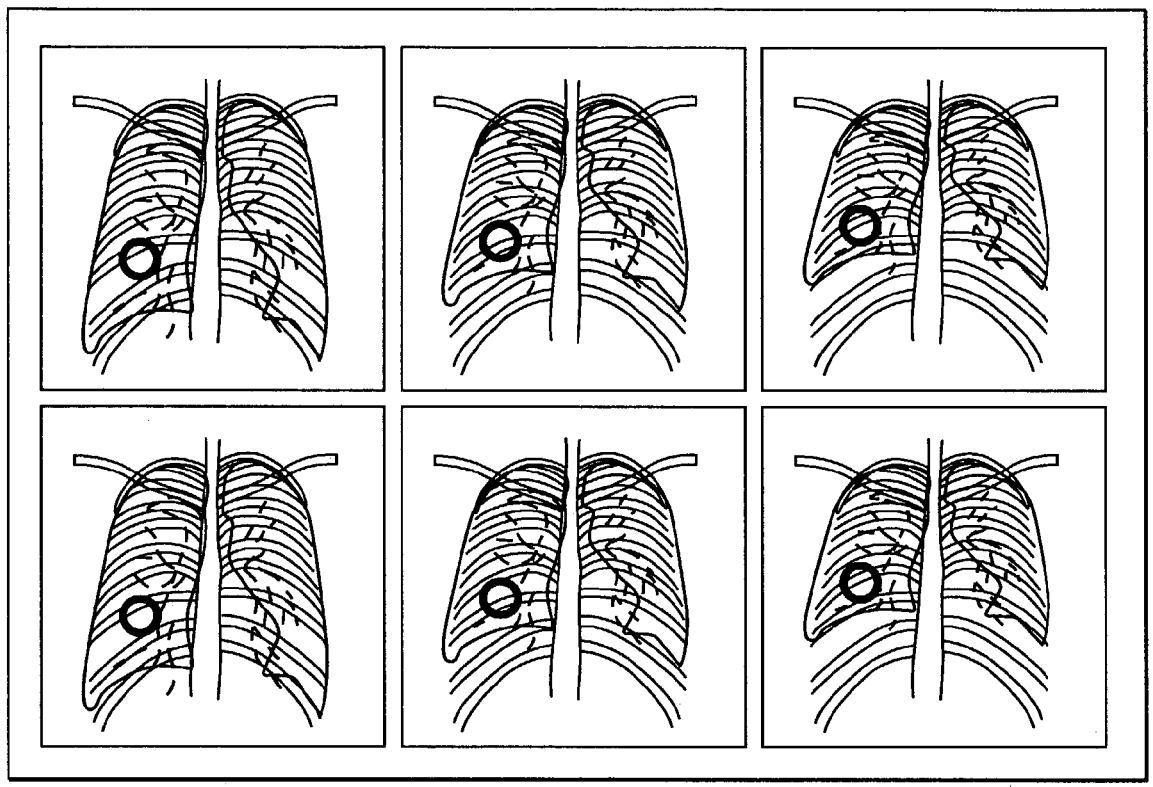
FIG. 11 schematically shows a set of examples of image frames according to a fourth embodiment, which are displayed side by side at the same time.

Instead of dynamically displaying the frames of moving-state image, the moving-state image data can also be displayed, as shown in FIG. 11, such that respective frame images constituting the moving-state image data are displayed (listed) side by side at the same time on one or a plurality of display units. In that case, one or more selected frames may be displayed instead of displaying all frame images. Also, in such listing display, the scaling-up and -down process may be incorporated to, for example, scale down each frame image. Further, when it is impossible or improper to display all of the frames at the same time, the frames may be displayed such that all of the frames can be observed while changing over or scrolling the screen.

(Fifth Embodiment)

Figure 12:
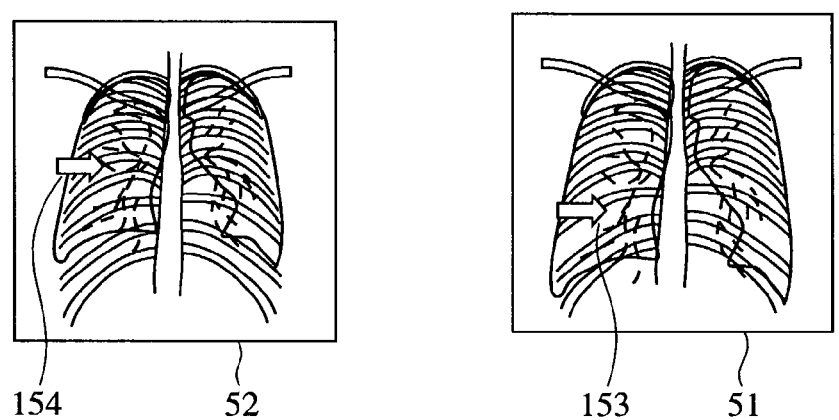
FIG. 12 schematically shows a set of examples of image frames representing a mark having a different shape according to a fifth embodiment.

FIG. 12 shows the case of employing a mark having a different shape from that shown in FIGS. 8 and 11. In FIG. 12, the mark has an arrow-like shape with the tip of the arrow pointing at the region of interest. In addition, the marking can also be realized, for example, by changing a display color between the region of interest and the remaining region, or embedding any other character, symbol, figure, etc., than those mentioned above in the image. In other words, any suitable manner capable of displaying a particular position or region on the image in a recognizable way can be employed.

Figure 13:
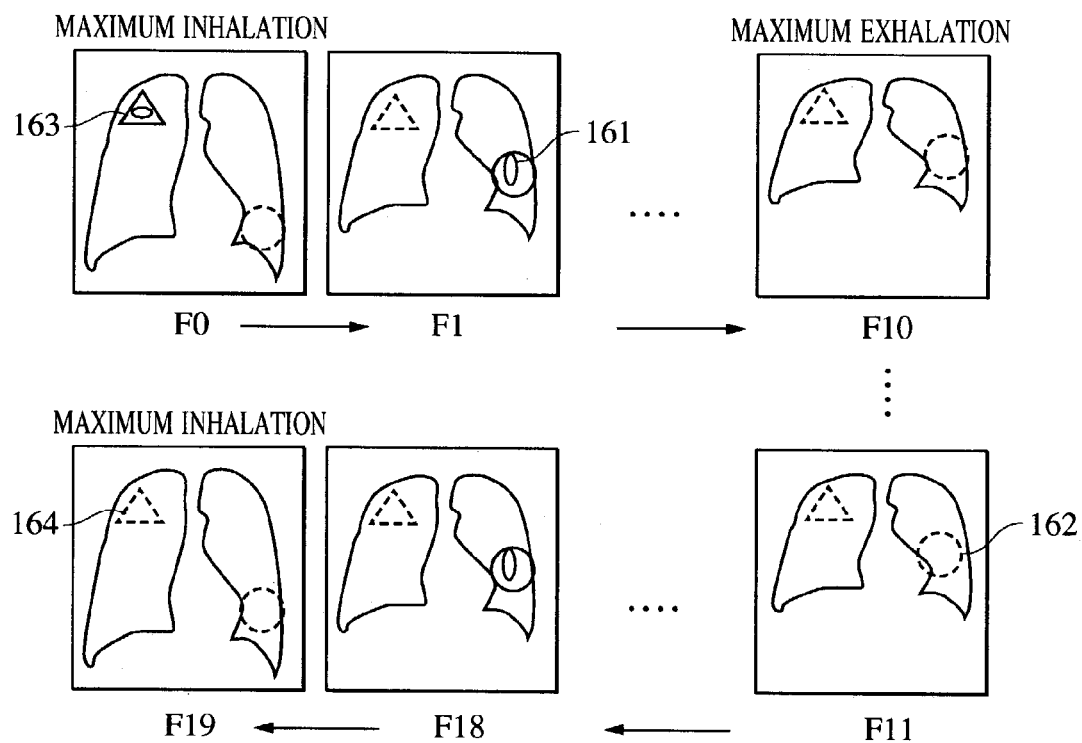
FIG. 13 schematically shows a set of examples of image frames representing the same location with marks of different shapes according to the fifth embodiment.

As still another example of the marking method, FIG. 13 shows the case in which, as a result of image analysis for detecting a disease candidate in each frame, one disease candidate is detected at the same location in frames F1, F18 and another disease candidate is detected at a different location only in a frame F0. In that case, marks 161, 162 having different forms are displayed to respectively indicate the target location in the relevant frames when one disease candidate is detected at the same location in the plural frames, and the corresponding location in the remaining frames in which that disease candidate is not detected. In this example, the mark 161 is a solid-line circle and the mark 162 is a dotted-line circle. However, any other suitable manner of marking is available so long as marks can be separately recognized. For example, colored marking may be employed such that the location corresponding to the mark 161 is displayed in one color and the location corresponding to the mark 162 is displayed in a different color. Further, the disease-candidate location detected only in one frame is not a genuine disease, with a high probability, and that location in the relevant frame is displayed using a mark 163 having a different form (solid-line triangle in this example). Then, a dotted-line triangle is used to indicate the corresponding location in the remaining frames in which that disease candidate is not detected in the location corresponding to the mark 163. By thus displaying marks having different forms in plural frames base on the image analysis result thereof, the image analysis result can be more effectively utilized for diagnosis.

(Sixth Embodiment)

The moving state image usable with the present invention is not limited to a radiographic image of the chest. In this sixth embodiment, a description is made of the case performing radiography of, as another example, a moving state image of the jaw joint (temporomandibular articulation).

Figure 14:
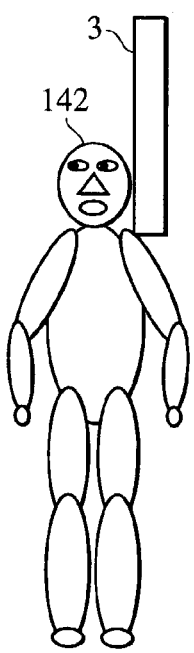
FIG. 14 schematically shows a manner of radiographing according to a sixth embodiment.

FIG. 14 shows a positional relationship between a head of a human body 142 and the flat panel detector 3. With such an arrangement, a moving state image of the jaw joint can be obtained using a similar apparatus or system to that shown in FIG. 1.

Figure 15:
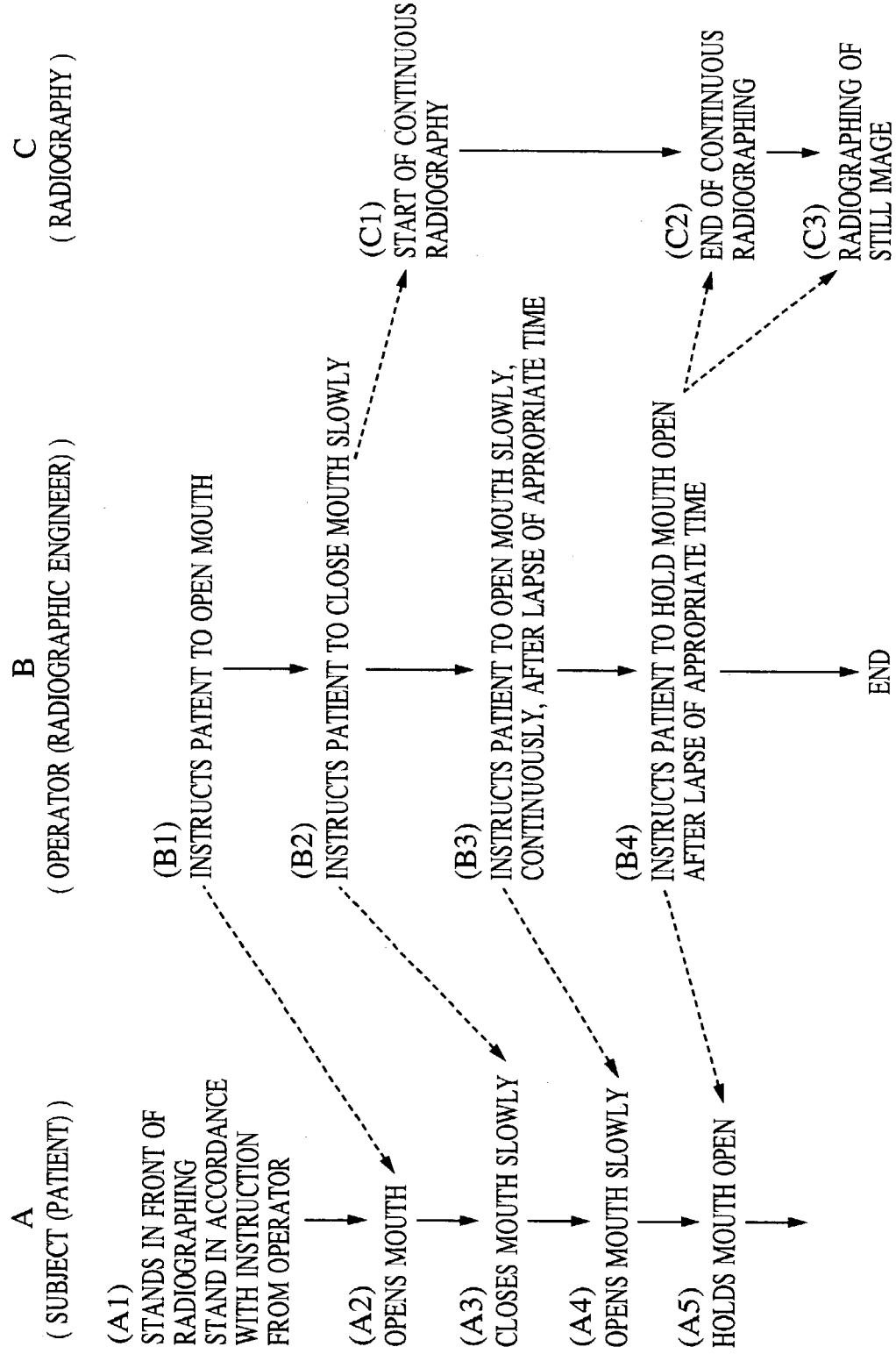
FIG. 15 is a chart showing a radiography sequence according to the sixth embodiment.

FIG. 15 shows a radiography sequence. The left-hand column A represents actions of a patient as a subject, the central column B represents actions of a radiographic engineer as an operator, and the right-hand column C represents a mode of a radiographing apparatus. At the first timing (A1), the patient stands in front of a radiographing stand (as denoted by 142 in FIG. 14) in accordance with an instruction from the operator. At the next timing (B1), the operator instructs the patient to open the mouth, and then to close the mouth slowly, from the timing (B2). In accordance with those instructions, the patient opens the mouth (A2), and then closes the mouth slowly (A3). In parallel, the operator operates the radiographing apparatus shown in FIG. 1 to start continuous radiography of the moving state of the patient's jaw joint (C1). An interval of the radiographing is about 3 to 10 image frames per second. After the lapse of an appropriate time (several seconds) while looking at the situation of the patient, the operator now instructs the patient to open the mouth slowly (B3). At this timing, the continuous radiography is still continued. While looking at the situation of the patient, when the patient has opened the mouth to the full, the operator instructs the patient to hold the mouth open (B4). At this timing, collection of continuous image data representing the moving state of the jaw joint is brought to an end (C2). Then, a radiograph of the state in which the patient holds the mouth open is taken as a still image (C3).

Figure 16:
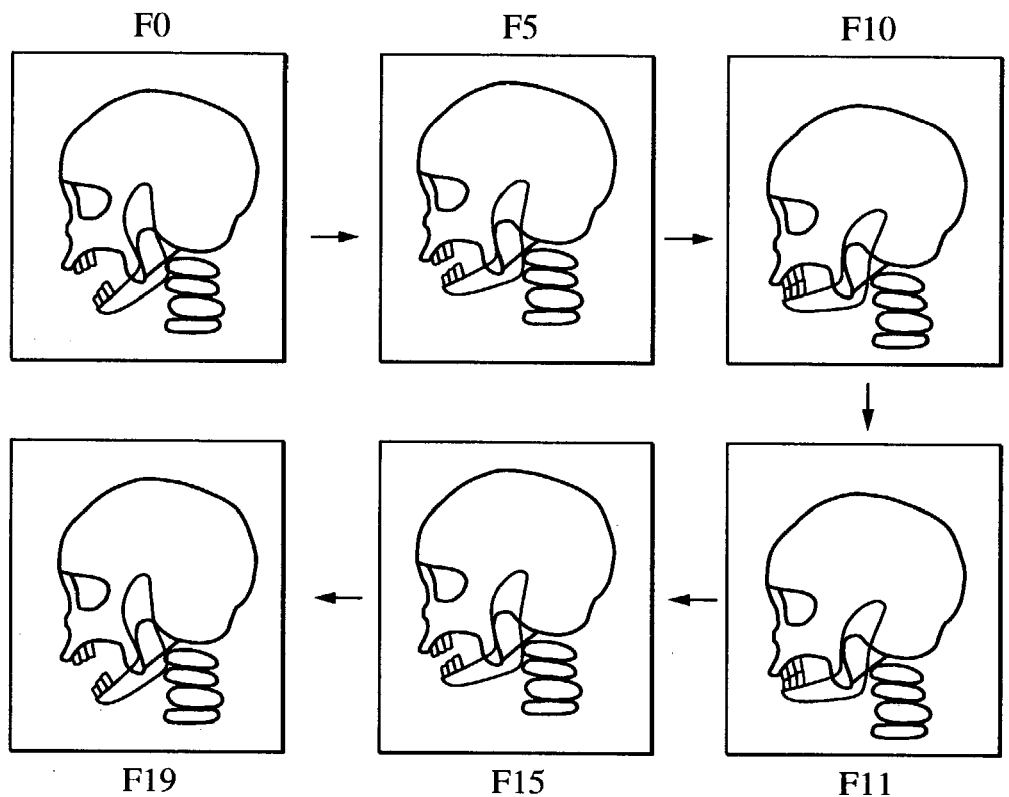
FIG. 16 schematically shows examples of image frames obtained according to the sixth embodiment.

Through the above sequence, the moving-state image of the jaw joint can be obtained as 20 frames of images F0 to F19, which are schematically shown in FIG. 16. For the moving-state image of the jaw joint, it is possible to carry out, e.g., image analysis for detecting the disease candidate for each frame, parallel display of both the moving-state image and the still image, positional correspondence, and marking in various forms, as with the above-described embodiments.

(Seventh Embodiment)

In this seventh embodiment, the limbs (extremities) are taken as another part of a human body of which a radiograph is to be taken, and the moving state of motions of a limb joint is analyzed.

Figure 17:
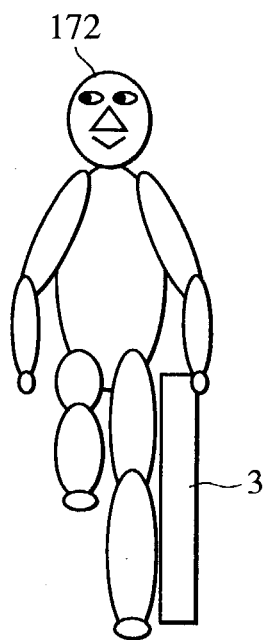
FIG. 17 schematically shows a manner of radiographing according to a seventh embodiment.

FIG. 17 shows one example of the positional relationship between a knee of a human body 172 and the flat panel detector 3. With such an arrangement, a moving state image of the knee joint can be obtained using a similar apparatus or system to that shown in FIG. 1. Performing radiography of the moving state of the knee joint of the standing patient is very effective in diagnosis of knee diseases because it means that the actual moving state of the knee joint can be observed in a condition under action of the gravity.

Figure 18:
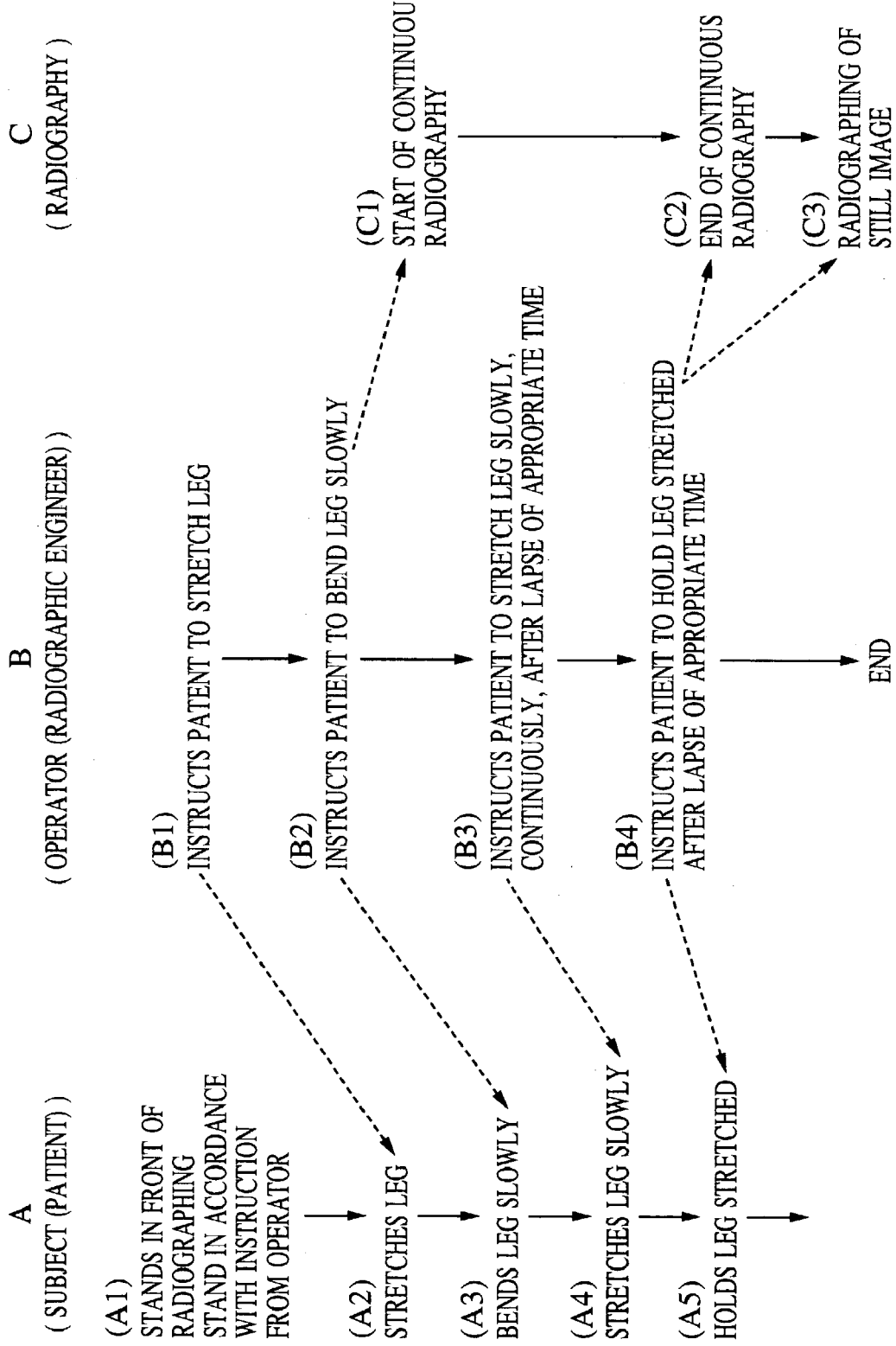
FIG. 18 is a chart showing a radiography sequence according to the seventh embodiment.

FIG. 18 shows a radiography sequence. The left-hand column A represents actions of a patient as a subject, the central column B represents actions of a radiographic engineer as an operator, and the right-hand column C represents a mode of a radiographing apparatus. At the first timing (A1), the patient stands in front of a radiographing stand (as denoted by 172 in FIG. 17) in accordance with an instruction from the operator. At the next timing (B1), the operator instructs the patient to stretch the leg in question, and then to bend the leg slowly from the timing (B2). In accordance with those instructions, the patient stretches the leg (A2), and then bends the leg slowly (A3). In parallel, the operator operates the radiographing apparatus shown in FIG. 1 to start continuous radiography of the moving state of the patient's knee joint (C1). An interval of the radiographing is about 3 to 10 image frames per second. After the lapse of an appropriate time (several seconds) while looking at the situation of the patient, the operator now instructs the patient to stretch the leg slowly (B3). At this timing, the continuous radiography is still continued. While looking at the situation of the patient, when the patient has stretched the leg to the full, the operator instructs the patient to hold the leg stretched (B4). At this timing, collection of continuous image data representing the moving state of the knee joint is brought to an end (C2). Then, a radiograph of the state in which the patient holds the leg stretched is taken as a still image (C3).

Figure 19:
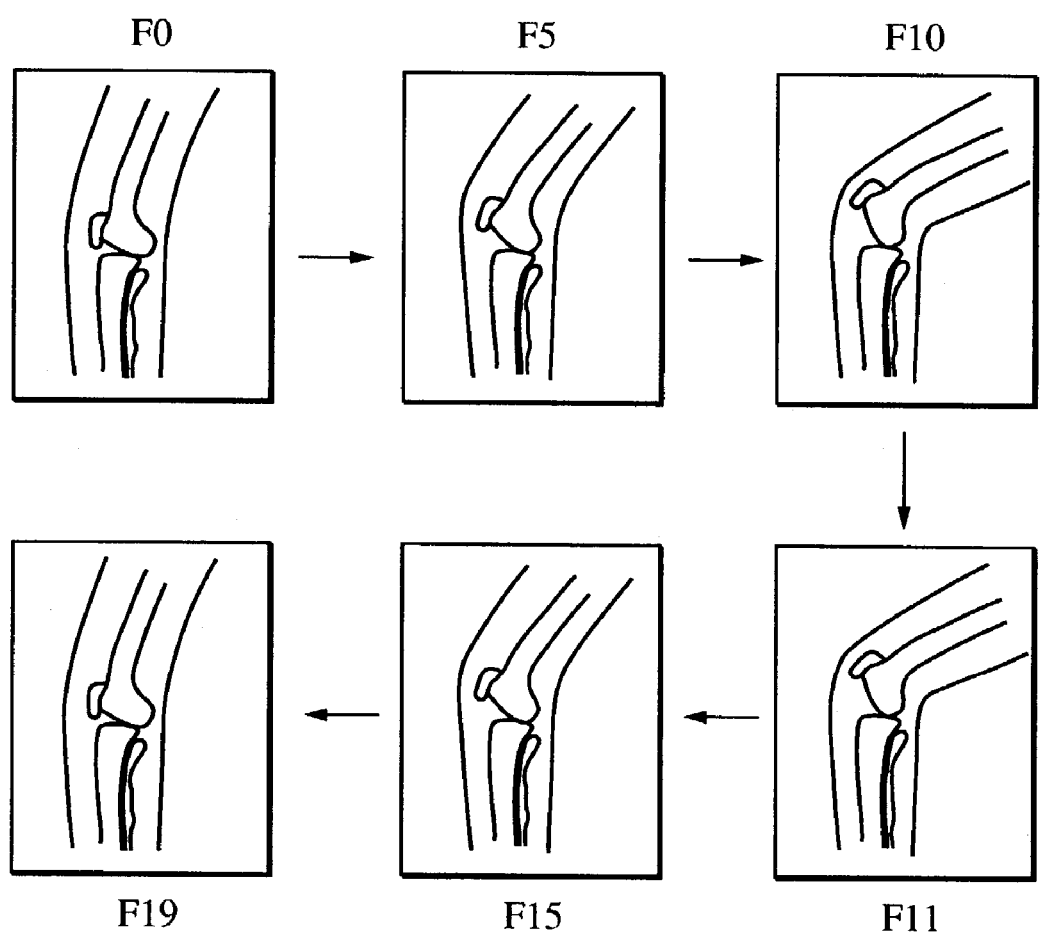
FIG. 19 schematically shows examples of image frames obtained according to the seventh embodiment.

Through the above sequence, the moving-state image of the knee joint can be obtained as 20 frames of images F0 to F19, which are schematically shown in FIG. 19. For the moving-state image of the knee joint, it is possible to carry out, e.g., image analysis for detecting the disease candidate for each frame, parallel display of both the moving-state image and the still image, positional correspondence, and marking in various forms, as with the above-described embodiments.

(Eighth Embodiment)

In this eighth embodiment, another example of performing radiography of moving state of the chest and analyzing an obtained radiograph of the moving state.

Figure 20:
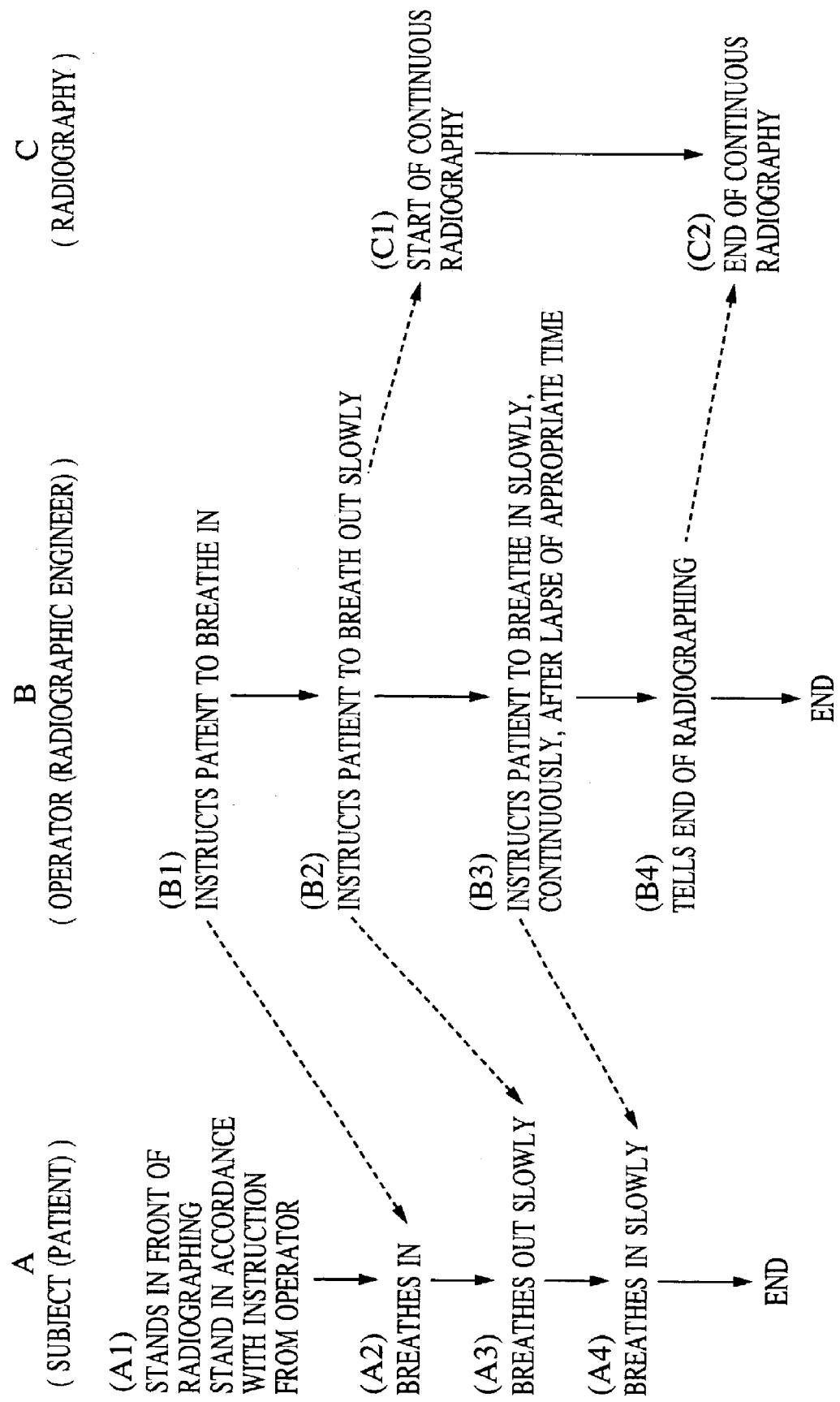
FIG. 20 is a chart showing one example of a radiography sequence according to an eighth embodiment.

FIG. 20 shows a radiography sequence. The left-hand column A represents actions of a patient as a subject, the central column B represents actions of a radiographic engineer as an operator, and the right-hand column C represents a mode of a radiographing apparatus. At the first timing (A1), the patient stands in front of a radiographing stand (as denoted by 2 in FIG. 1) in accordance with an instruction from the operator. At the next timing (B1), the operator instructs the patient to breathe in, and then to breathe out slowly from the timing (B2). In accordance with those instructions, the patient breathes in (A2), and then breathes out slowly (A3). In parallel, the operator operates the radiographing apparatus shown in FIG. 1 to start continuous radiography of the moving state of the patient chest in breathing (C1). An interval of the radiographing is about 3 to 10 image frames per second. After the lapse of an appropriate time (several seconds) while looking at the situation of the patient, the operator now instructs the patient to breathe in slowly (B3). At this timing, the continuous radiography is still continued. While looking at the situation of the patient, when the patient has breathed in to the full, the operator advises the patient of the end of the radiography (B4). Collection of continuous image data representing the moving state in breathing is then brought to an end (C2).

Figure 21:
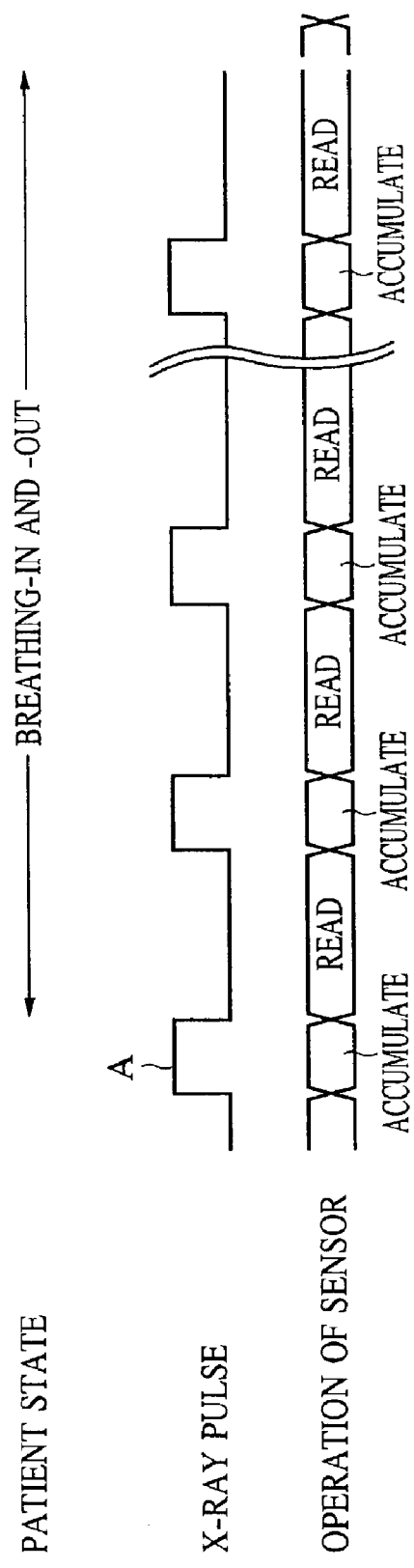
FIG. 21 is a timing chart for the radiography sequence.

FIG. 21 is a timing chart schematically showing the radiography sequence. The upper row represents the patient state, the middle row represents an X-ray pulse, and the lower row represents the operation of a sensor system including the flat panel detector 3. While the patient breathes in and out in accordance with the instructions from the operator, an X-ray pulse with a magnitude A is repeatedly issued. During a period in which the X-ray pulse is being issued, the sensor system accumulates image information, and during the remaining period, it reads the accumulated image information. The pulse width or magnitude A of each X-ray pulse may be set to a predetermined constant value, or may be controlled using the photo-timer 4 shown in FIG. 1. In such a case, when a total amount (integrated value) of X-rays measured by the photo-timer 4 reaches a predetermined value, the controller 15 sends an X-ray radiation stop signal to the X-ray generator 1, thereby stopping the X-ray radiation (i.e., terminating the pulse).

With the above-described operations, radiographs of the moving state in breathing can be taken while the patient is instructed to perform actions that are not much different from the action required in conventional health diagnosis, i.e., just slow deep breathing.

The order and the number of times of breathing in and out are not limited to those ones described above as this eighth embodiment.

Further, with the above-described operations, the moving state image made up of plural frames corresponding to respective phases in breathing of the patient can be obtained.

Other examples of the operation executed in the analysis and display block 22 in FIG. 1 will be described below. The CAD process is first described and three examples of this eighth embodiment are then described.

Figure 22:
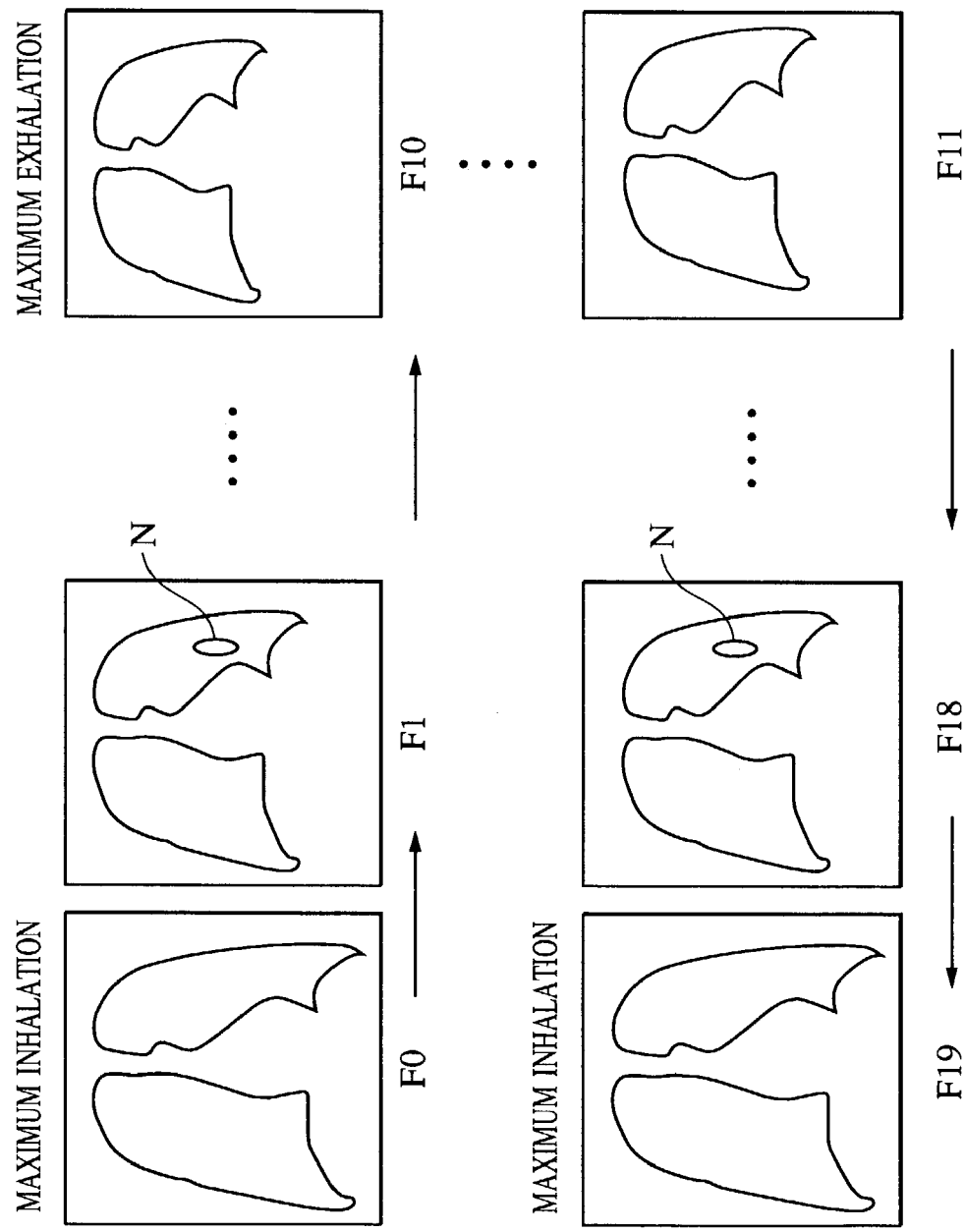
FIG. 22 schematically shows the case in which a disease candidate is detected from frames of moving state images in breathing.

Hitherto, the CAD process has been performed using an image of the patient's chest in the maximum inhalation state. However, the shadow of a tremor or the like is not always most easily observed in the maximum-inhalation state, and it is more easily observed at a certain particular phase in breathing in some cases. That phenomenon also depends on a change in the radiographing angle of the patient and the positional relationship with respect to blood vessels, bones, etc. In this embodiment, the image analysis with the conventional CAD made on the still image is performed on each of the image frames of respective breathing phases in an independent way. FIG. 22 schematically shows, by way of example, a set of results of image analysis carried out on the image frames of respective breathing phases for detecting a disease-suspicious sign (disease candidate). In FIG. 22, some disease-suspicious sign is detected only in image frames F1 and F18 at a position (referred to also as a "region of interest") indicated by N. Those results could not be clearly detected if the image analysis were carried out only on image frames F0 or F19 obtained in the maximum-inhalation state, as is conventional.

Thus, a larger amount of information, which has not been obtained in the past, can be obtained just by taking a plurality of radiographic images of a moving respiratory state instead of taking a plurality of radiographic images of the patient at different angles. Correspondingly, the amount of information available in the CAD process is increased and the accuracy of the CAD process is improved.

The following is a description of three examples of this embodiment with regard to the CAD process mentioned above.

EXAMPLE 1

Figure 23:
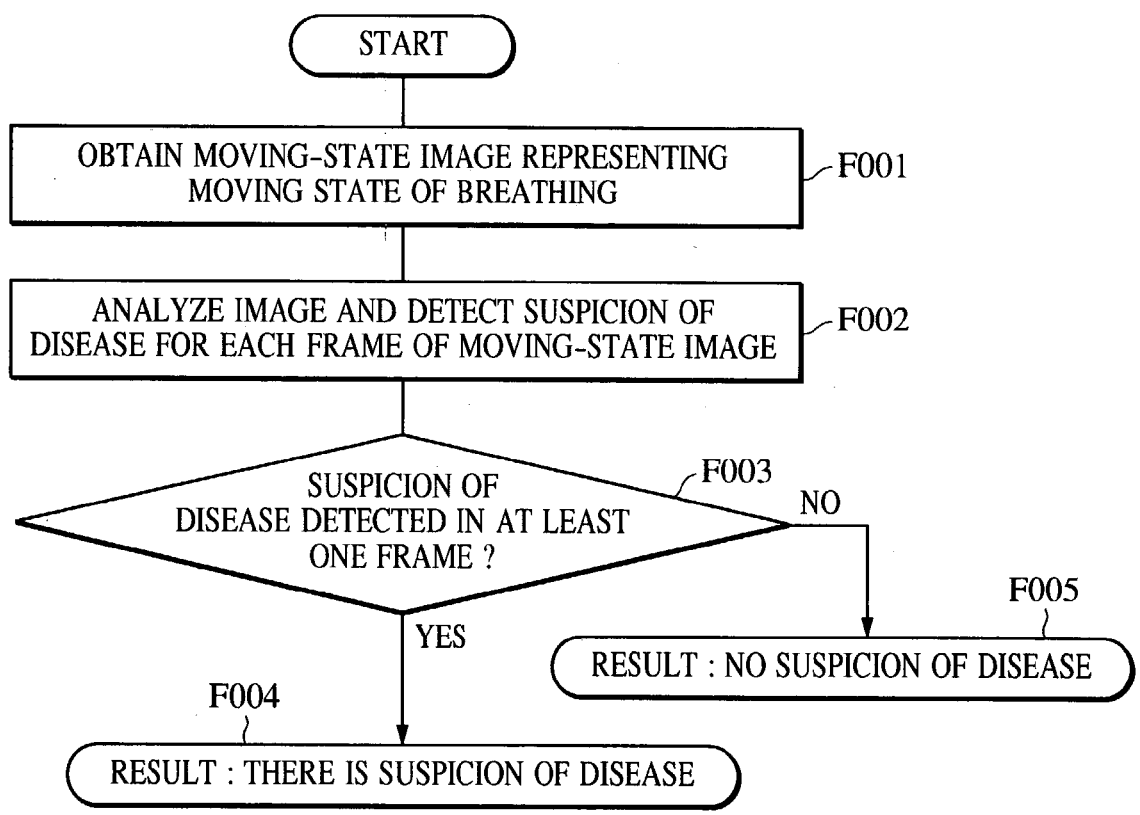
FIG. 23 is a flowchart showing the operation of Example 1.

FIG. 23 is a flowchart showing the processing executed in this Example 1. In step F001, a moving-state image representing the moving state in breathing is obtained in the same manner as that described above. A plurality of image frames are obtained in this step F001. In step F002, the image analysis for detecting the disease-suspicious sign, which has been made on a still image in the past, is carried out on each frame to detect a disease-suspicious location (referred to also as a "region of interest") in each image frame. If the disease-suspicious sign is detected in at least one frame in determination step F003 as a result of the step F002, the process flow advances to step F004, in which a message indicating the suspicion of a disease is output (displayed). Only when no disease-suspicious sign is detected as a result of the step F003, the process flow advances to step F005, in which a message indicating no suspicion of a disease is output.

In this Example 1, if there is any suspicion of a disease, the detected result indicating the suspicion of a disease is reported to the doctor, i.e., the diagnosing person. In accordance with such a report, the doctor is able to observe the image again or to instruct a close examination. In this Example 1, since the image frames in which the disease-suspicious sign has been detected are all output, the discovery rate of diseases is increased, but the case in which there is actually no disease is also reported as being suspicious, and the number of close diagnosis to be made by the doctor in a later state is increased. Therefore, this method is suitable as CAD processing for health diagnosis in which missing a case of disease must be avoided as far as possible.

Further, in this Example 1, it is not necessarily required to carry out the image analysis to detect the disease-suspicious sign for all of the image frames. A diagnosis result can also be obtained by carrying out the image analysis for a part of the image frames rather than all of them.

Although the step F003 in FIG. 23 determines "whether the disease-suspicious sign is detected in at least one frame", the strictness in criteria for disease detection can be varied by changing the number of frames determined in the step F003. For example, the detection criteria may be modified such that if the disease candidate is detected in images amounting to 20% or more of the total number of frames, a message indicating the suspicion of a disease is output.

EXAMPLE 2

Figure 24:
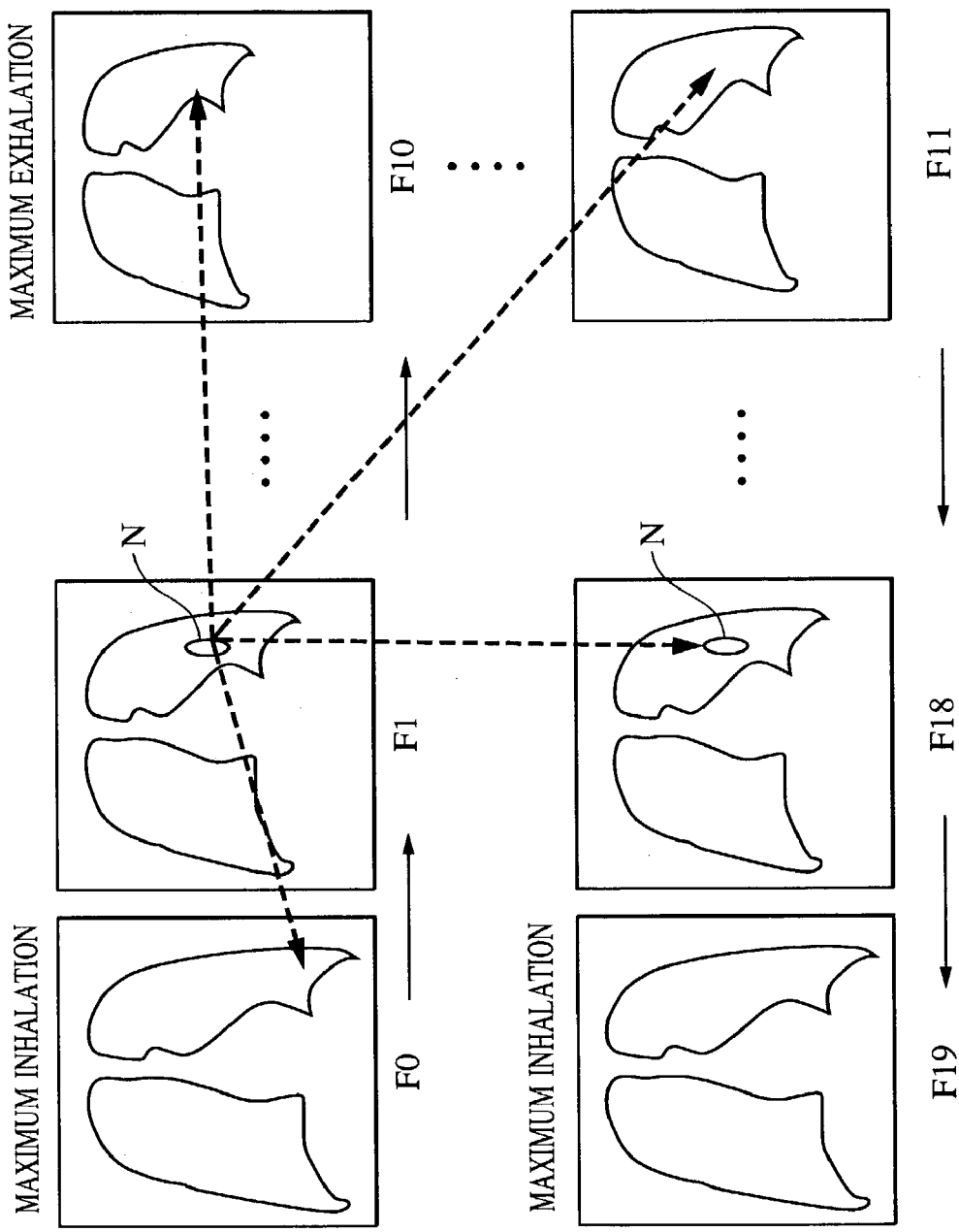
FIG. 24 schematically shows a group of image frames representing regions corresponding to a region in which a disease candidate has been detected.

This Example 2 is basically similar to Example 1, but differs from it in that the disease-suspicious location (referred to also as the "region of interest") is indicated as an output result on all of the frames. While FIG. 22 shows the case in which the disease candidate is detected in the frames F1 and F18, the corresponding region in each of other frames can be easily specified if the images are labeled based on motion vectors as shown in FIG. 7. Thus, as shown in FIG. 24, the region in each of other frames corresponding to the disease-candidate region detected in the frame F1 can be easily specified based on the label.

There is a possibility that the disease sign appears on other frames as well, but it cannot be detected with the detection capability of the conventional CAD process executed on a still image.

Figure 25:
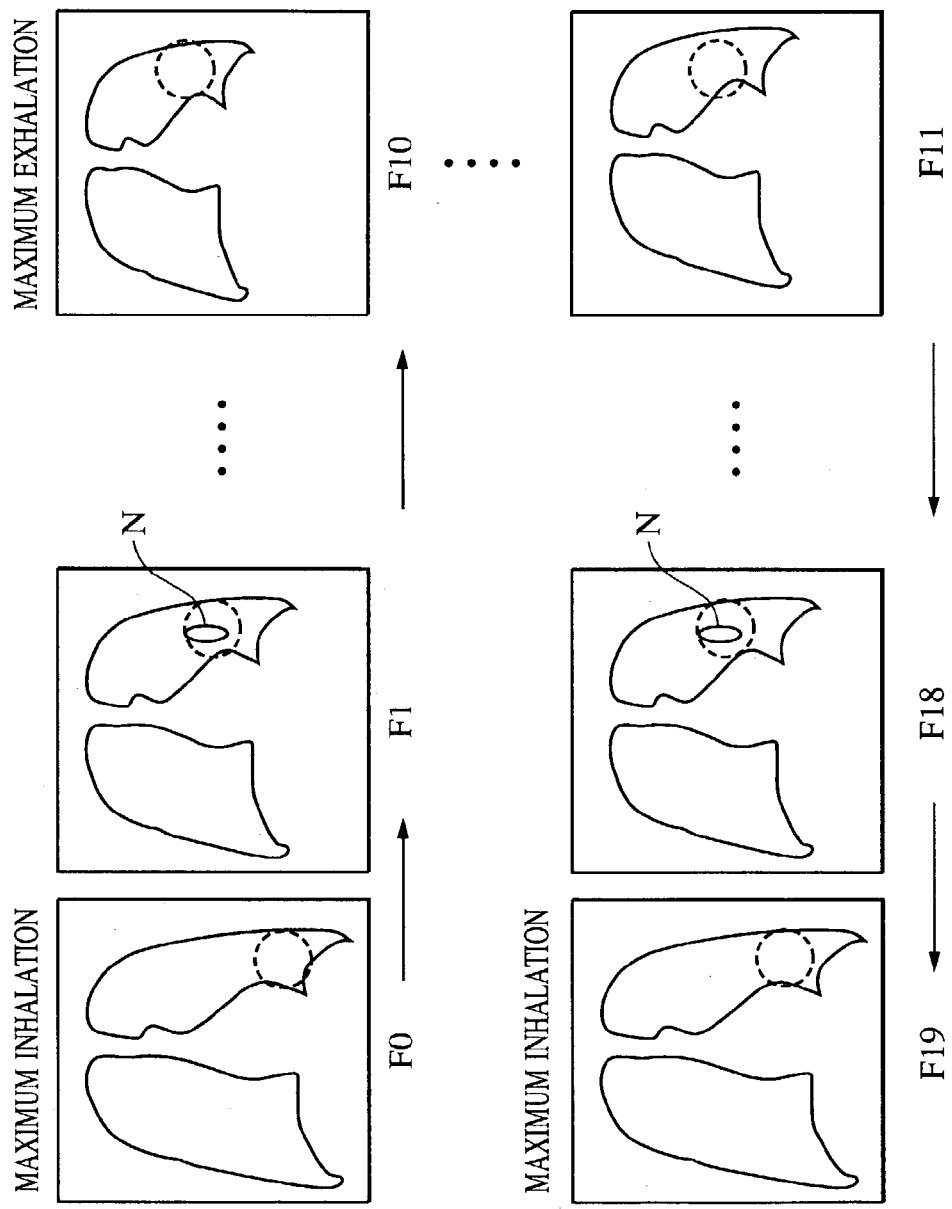
FIG. 25 schematically shows a group of image frames representing an example of display of regions corresponding to a region in which a disease candidate has been detected.

Taking into account such a possibility, in this Example 2, the region in each of other frames corresponding to the disease-candidate region is displayed as the disease-suspicious region, thereby prompting the doctor, i.e., the diagnosing person, to pay attention to it. More specifically, FIG. 25 shows, by way of example, a set of image frames presented to the doctor. While looking at the moving state image, the doctor can easily confirm the disease-suspicious region, which has been presented as a result of the CAD process, in all of the frames based on the disease candidate detected in at least one frame. Hence, the doctor is able more closely to observe and diagnoses the disease-suspicious region.

Further, in this Example 2, it is not necessarily required to carry out the image analysis to detect the disease-suspicious sign for all of the image frames. A diagnosis result can also be obtained by carrying out the image analysis for a part of the image frames rather than all of them.

EXAMPLE 3

This Example 3 is premised on the detection accuracy of the image analysis for detecting any suspicion of a disease, being variable, or on a plurality of image analysis algorithms being usable. The disease-candidate region recognized in Example 2 is not detected in the first image frame, but it may be detected by increasing the detection accuracy of the CAD process (image analysis) or by employing another image analysis algorithm. Taking into account that case, in this Example 3, if any suspicion of a disease is detected in at least one frame, another image analysis algorithm with higher accuracy is applied to the corresponding region in each of other frames, and if no suspicion of a disease is detected as a result of the image analysis, it is determined that the suspicion of a disease first detected does not indicate an actual disease.

Figure 26:
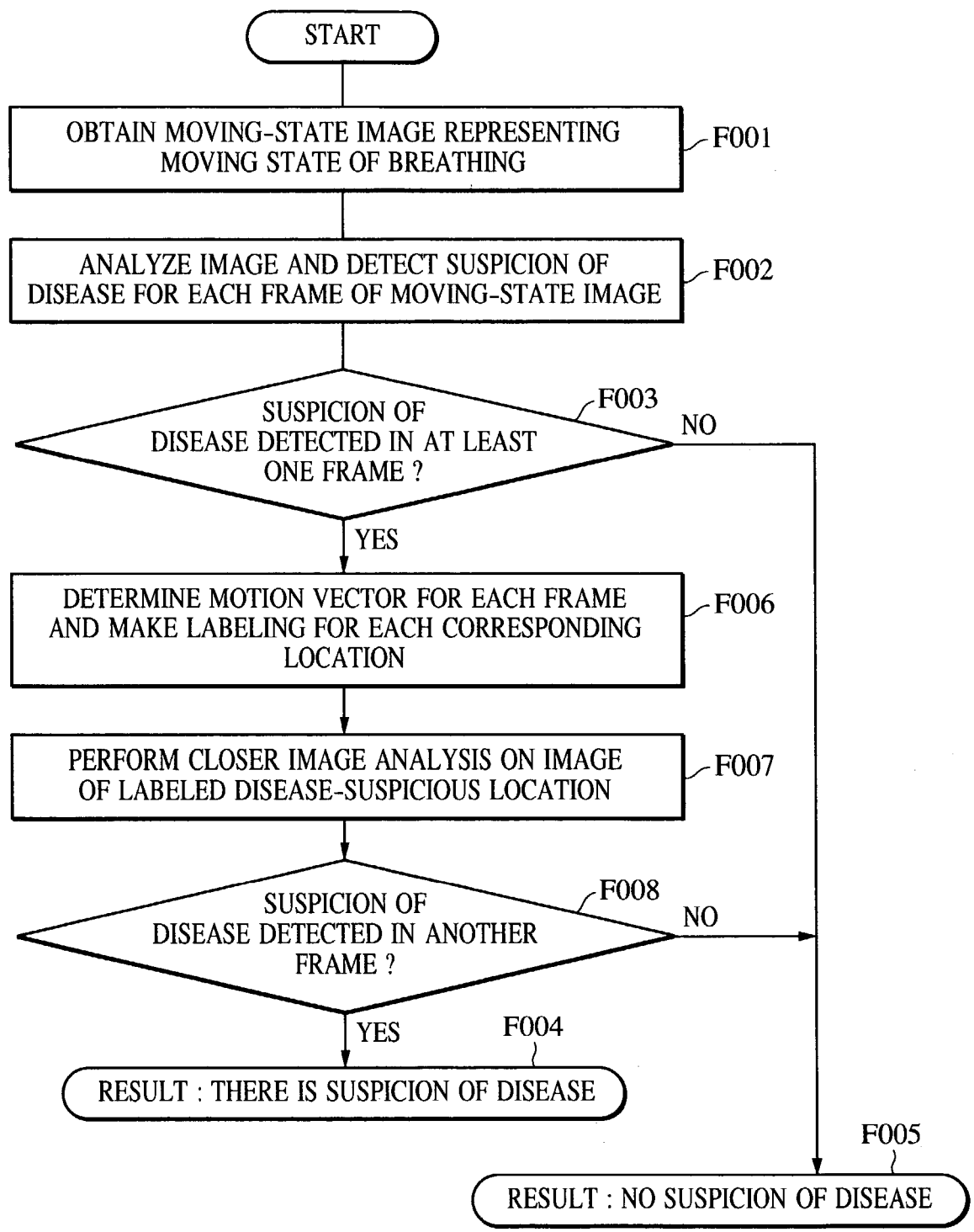
FIG. 26 is a flowchart showing the operation of Example 3.

FIG. 26 is a flowchart showing the processing executed in this Example 3. Steps F001 to F003 are the same as those in FIG. 23 and hence are not described here. If any suspicion of a disease is detected in at least one frame, the process flow advances to step F006 in which labeling is made on corresponding regions of all the frames based on motion vectors determined for each frame, and the label indicating the disease-suspicious region is extracted. In step F007, closer image analysis is carried out on the labeled disease-suspicious region. If it is determined in step F008 as a result of the image analysis in the step F007 that the suspicion of a disease is detected in another frame as well, the process flow advances to step F004. If not so detected, the process flow advances to step F005. Step F004 outputs a message indicating the suspicion of a disease, and step F005 outputs a message indicating no suspicion of a disease, based on judgment that the suspicion of a disease first detected was false. The method of this Example 3 is intended to avoid the false detection of suspicion of a disease and is effective in reducing the number of patients who are diagnosed as possibly suffering from any disease in spite of actually being healthy and are instructed to take closer examination. Generally, image analysis conducted so as to detect disease candidates with high accuracy has problems in that it takes a long processing time and detects an excessively large number of disease candidates (i.e., gives an onerously large number of false positives). In view of those problems, by setting the accuracy level (or the algorithm to be used) to be variable and carrying out the highly-accurate image analysis on not all the area of the image, but only the region of each image corresponding to the disease-suspicious region detected in another frame, the CAD process can be more effectively executed at higher speed.

Further, in this Example 3, it is not necessarily required to carry out the image analysis to detect the disease-suspicious sign(s) for all of the image frames. A diagnosis result can also be obtained by carrying out the image analysis for just a portion of the image frames rather than all of them.

Other Embodiments

The object of the present invention can also be achieved by supplying a storage medium, which stores program codes of software for realizing the functions of the apparatus or system according to any of the above-described first to eighth embodiments, to the apparatus or system, and causing a computer (CPU or MPU) in the apparatus or system to read and execute the program codes stored in the storage medium.

In that case, the program codes read out of the storage medium serve in themselves to realize the functions of any of the above-described first to eighth embodiments, and hence the storage medium storing the program codes and the program codes themselves constitute the present invention.

Storage mediums for supplying the program codes may be, e.g., ROMs, Floppy (trade name) disks, hard disks, optical disks, magneto-optical disks, CD-ROMs, CD-Rs, magnetic tapes, and nonvolatile memory cards.

Also, the functions of any of the above-described first to eighth embodiments are realized not only by a computer executing program codes read out of the storage medium, but also by an Operating System (OS) or the like which is running on the computer and executes a part or the whole of the actual processing in accordance with commands from the program codes, thereby realizing the functions of any of the above-described first to eighth embodiments. Those cases are also of course included in embodiments of the present invention.

Further, the present invention involves a case in which program codes read out of the storage medium are written in a memory provided in a function add-on board inserted in the computer or a function add-on unit connected to the computer, and a CPU or the like incorporated in the function add-on board or unit executes a part or the whole of the actual processing in accordance with commands from the program codes, thereby realizing the functions of any of the above-described first to eighth embodiments.

When the present invention is applied to such a program or a storage medium storing the program, the program is made up of program codes corresponding to, e.g., the flowcharts shown in FIGS. 4, 9, 10, 23 and/or 26.

Figure 27:
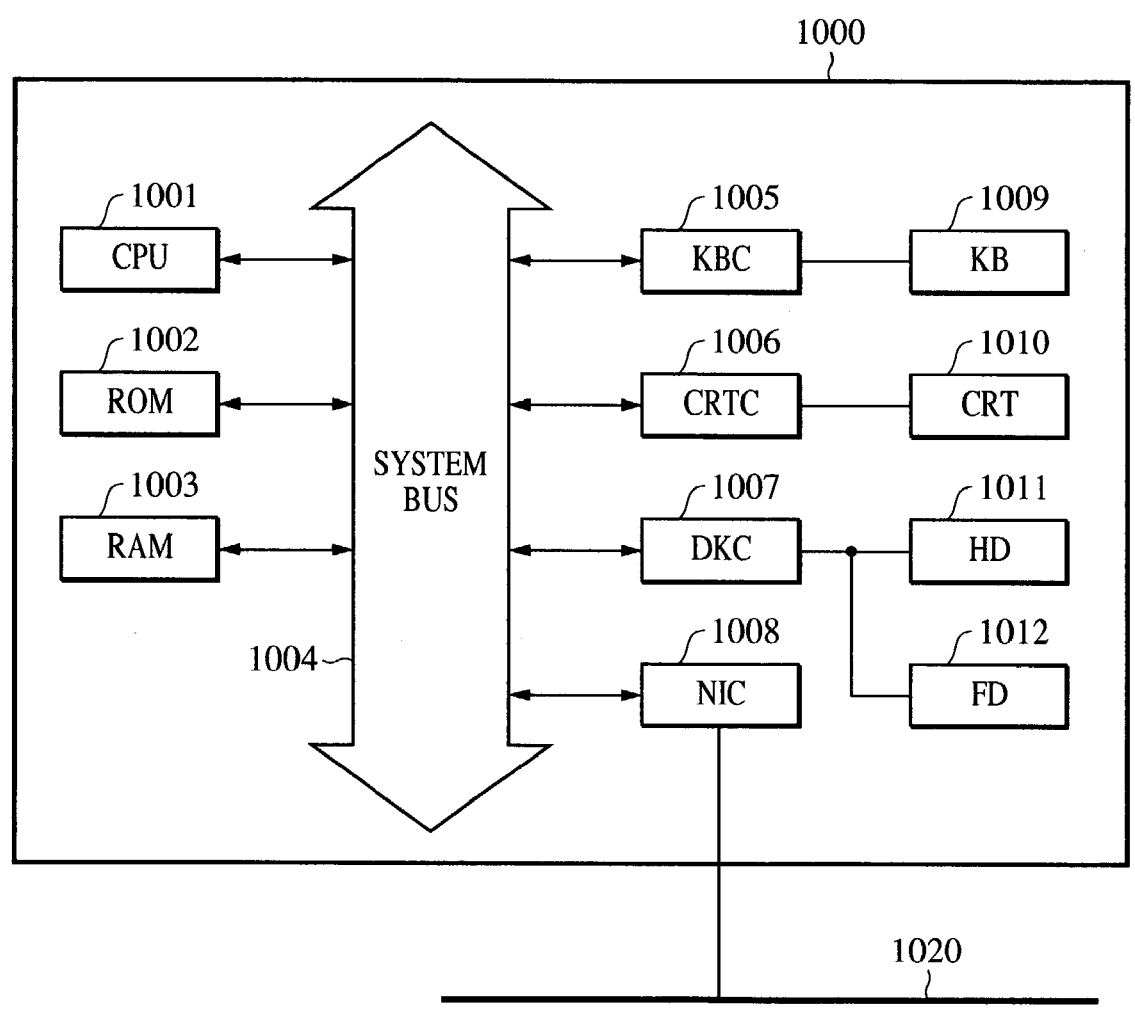
FIG. 27 is a block diagram showing a configuration of a program executable computer according to the functions or the operation of the embodiment.

FIG. 27 shows a configuration of a computer 1000 for use in the above-described embodiments.

As shown in FIG. 27, the computer 1000 comprises a CPU 1001, a ROM 1002, a RAM 1003, a keyboard controller (KBC) 1005 for controlling a keyboard (KB) 1009, a CRT controller (CRTC) 1006 for controlling a CRT display (CRT) 1010 serving as a display unit, a disk controller (DKC) 1007 for controlling a hard disk (HD) 1011 and a Floppy (trade name) disk (FD) 1012, and a network interface controller (NIC) 1008 for connection with a network 1020. These components are interconnected via a system bus 1004 in a mutually communicable manner.

The CPU 1001 executes software stored in the ROM 1002 or the HD 1011, or software supplied from the FD 1012, and controls the respective components connected to the system bus 1004 in a supervising manner.

In other words, the CPU 1001 reads and executes, from the ROM 1002, the HD 1011 or the FD 1012, a processing program in accordance with a predetermined processing sequence, thereby carrying out control to realized the operations of the above-described first to third embodiments.

The RAM 1003 functions as a main memory, a work area or the like for the CPU 1001. The KBC 1005 makes control regarding command inputs from the KB 1009, a not-shown pointing device, etc. The CRTC 1006 makes control regarding display on the CRT 1010.

The DKC 1007 makes control regarding access to the HD 1011 and the FD 1012 storing, e.g., a boot program, various applications, an editing file, a user file, a network management program, and a predetermined processing program.

The NIC 1008 exchanges data, etc., in two-way directions with respect to the apparatus or system on the network 1020.

As a matter of course, the present invention is applicable not only to a system comprising plural pieces of equipment (such as a radiation generator, a radiographing apparatus, an image processor, and an interface unit), but also to one piece of equipment in which the functions of those units are incorporated together. When the present invention is applied to a system comprising plural pieces of equipment, those plural pieces of equipment are interconnected via, e.g., an electrical connecting unit (such as a communicating unit), an optical connecting unit (such as a communicating unit), and/or a mechanical connecting unit.

Figure 28:
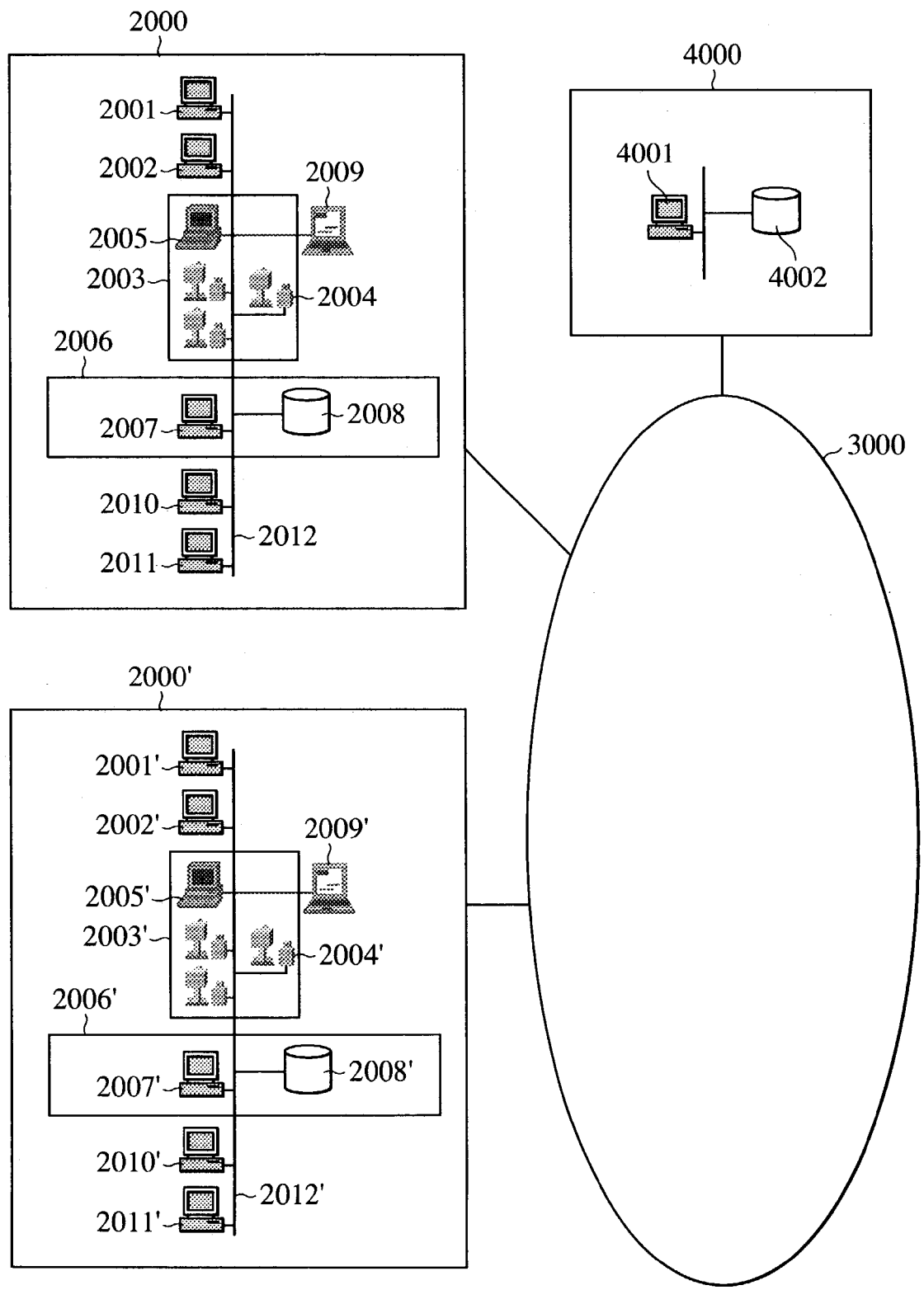
FIG. 28 is a block diagram for explaining an embodiment in which the present invention is applied to a system operating via a network.

Further, the present invention is applicable to a system operating via a network (such as a LAN and/or a WAN) as shown in FIG. 28. Referring to FIG. 28, a medical facility 2000 has a hospital information system (HIS) 2001 including a computer, a computer network or the like to manage information (such as clinical chart information, check information, and counting information) regarding patients who have visited the medical facility 2000. Numeral 2002 denotes a radiological department information system (RIS) including a computer, a computer network or the like to manage information related to the radiological department. The RIS 2002 cooperates with a radiographing system 2003 (described later) to manage, e.g., information requested for radiographing from the HIS.

The medical facility 2000 further includes the radiographing system 2003 for taking radiographs. The radiographing system 2003 comprises, e.g., one or more radiographing apparatuses 2004 for taking radiographs of patients and outputting image data, and a radiography management/image processing server 2005 for performing management of radiography and image processing of radiographs in accordance with, e.g., the radiographing request information from the RIS. Note that the radiographing system 2003 or the radiographing apparatus 2004 includes, for example, the above-described apparatus or system shown in FIG. 1.

A picture archiving communication system (PACS) 2006 has, e.g., the functions of archiving image data from the radiographing system 2003 along with information necessary for management of the image data and/or image analysis, etc. (referred to also as "associated information"), and providing the image data (and the associated information) as required. The PACS 2006 comprises, for example, a PACS server 2007 including a computer, a computer network or the like, and an image storage 2008 for storing the image data and the associated information.

A diagnosis request management system 2009 cooperates the radiographing system 2003 and/or the PACS 2006, etc., not only to transmit, to the diagnosing doctor, diagnosis request information regarding the image data from the radiographing system 2003 automatically or in accordance with an operation of the operator (e.g., a radiographic engineer) for providing the image data for the image diagnosis (i.e., reading of the image data by the diagnosing doctor), but also to manage the progress of image diagnosis. The diagnosis request management system 2009 includes a computer, a computer network or the like.

Diagnosis terminals (image viewers or the like) 2010, 2011 used by the diagnosing doctor includes a computer, a computer network or the like which has, e.g., the functions of receiving the diagnosis request information from the diagnosis request management system 2009, obtaining the image data and the associated information from the PACS 2006, entering diagnosis results by the diagnosing doctor, and transmitting information of the diagnosis results and/or information indicating the end of diagnosis to the diagnosis request management system 2009.

The above-mentioned components 2001 to 2011 are interconnected via a LAN (Local Area Network) 2012. Also, the diagnosis result information is directly transmitted from the diagnosis request management system 2009 or the diagnosis terminal 2010, 2011 to at least one of the hospital information system 2001, the radiological department information system 2002, and the PACS 2006.

The destination of the diagnosis request from the diagnosis request management system 2009 is not limited to the interior of the medical facility 2000 to which the system 2009 belongs. For example, it is also possible to request diagnosis to the diagnosing doctor in another medical facility via a WAN (Wide Area Network) utilizing a public telephone line or a dedicated line. FIG. 28 shows the case in which the medical facility 2000 is connected to another medical facility 2000' via a network 3000. In FIG. 28, the medical facility 2000' is shown as including the same components 2001' to 2012' as those in the medical facility 2000, the construction of the medical facility 2000' is not limited to the illustrated one. The diagnosis request management system 2009 of the medical facility 2000 is able to, for example, request diagnosis to the medical facility 2000' via the Internet 3000 and then the diagnosis request management system 2009' of the medical facility 2000', and to obtain a diagnosis result from the medical facility 2000'.

Also, instead of the above-described system for directly communicating the diagnosis request information, the image data, the diagnosis result information, etc. between the medical facilities, a system may be constructed so as to carry out similar processing via a diagnosis intermediating facility 4000. In that case, for example, the diagnosis request management system 2009 of the medical facility 2000 transmits the diagnosis request information, including the image data, to the diagnosis intermediating facility 4000 via the Internet 3000. The diagnosis intermediating facility 4000 is a facility belonging to a diagnosis intermediating service agency (e.g., a diagnosis intermediating service company), and it comprises, for example, an intermediating server 4001 including a computer, a computer network or the like, and a storage 4002 for storing necessary data.

The intermediating server 4001 has, e.g., the function of selecting the medical facility and/or the diagnosing doctor suitable for diagnosis based on the diagnosis request information from the medical facility 2000, the function of transmitting the diagnosis request information to the selected medical facility and/or diagnosing doctor, the function of transmitting the image data, etc., required for the diagnosis to the selected medical facility and/or diagnosing doctor, the function of obtaining the diagnosis result information from the selected medical facility and/or diagnosing doctor, and the function of providing the diagnosis result information, etc., to the medical facility 2000. The storage 4002 stores not only the diagnosis request information, but also data necessary for executing those functions, e.g., data necessary for selecting the medical facility and/or the diagnosing doctor suitable for the diagnosis (such as data regarding the network address, diagnostic field, diagnostic capability, and schedule of the medical facility and/or the diagnosing doctor). With that system configuration, the diagnosis request management system 2009 of the medical facility 2000 is able to receive the diagnosis result information from the medical facility and/or the diagnosing doctor suitable for the diagnosis request information via the Internet 3000 and the diagnosis intermediating facility 4000.

The medical facility 2000 is not limited to a medical organization such as a hospital, but it may be, e.g., a health screening organization in which the diagnosing doctor is engaged. In that case, the medical facility 2000 is substituted with a health screening organization 2000" (not shown) made up of similar components to those 2003 to 2012 described above. Also, the medical facility 2000 may be an examination organization in which only examination (e.g., radiography) is carried out. In that case, the medical facility 2000 is substituted with, e.g., an examination organization 2000''' (not shown) made up of similar components to those 2003 to 2009 and 2012 described above.

Further, the system, apparatus, means or function (e.g., the analysis and display block 22 in the radiographing system 2003 or the radiographing apparatus 2004, or a part of the block 22) is not necessarily prepared within the medical facility 2000, but it may be instead provided by a similar or analogous system, apparatus, means or function in another facility via, e.g., the Internet 3000.

A flow of processing executed by the radiographing system 2003 and the diagnosis request management system 2009 in the medical facility 2000 will be described below. First, a flow of processing executed by the radiographing system 2003 is described with reference to a flowchart of FIG. 29. In step S5001, the radiographing system 2003 determines whether there is radiographing request information transmitted from the HIS or RIS. If the radiographing request information is present, the process flow advances to step S5003, and if it is not present, the process flow advances to step S5002. In step S5002, it is determined whether there is an instruction to end the operation of the radiographing system 2003. If the end of the operation is instructed, the radiographing system 2003 brings the operation to an end. If the end of the operation is not instructed, the radiographing system 2003 returns to step S5001 and continues the operation. In the step S5003, the radiographing system 2003 executes radiographing in accordance with the radiographing request information in a manner similar to that described above in connection with the embodiments.

After executing the radiography, it is determined whether the radiography requested for one patient (subject) has been fully completed (step S5004). If the radiography is not yet completed, the radiographing system 2003 starts image processing of a radiographic image, which has been taken in the previous radiographing cycle, in step S5005 and then returns to the step S5003 to continue the radiography process. The image processing is executed in the same manner as that described above in connection with the embodiments, and is carried out in parallel to the radiography in the step S5003. If the radiography for the relevant patient is fully completed, the process flow advances to step S5006.

In step S5006, it is determined whether the image processing is completed for all of the radiographs of the relevant patient obtained by the radiography. If the image processing is all completed, the process flow advances to step S5007, and if the image processing is not yet completed, the determination in step S5006 is repeated.

In step S5007, the radiographing system 2003 starts transmission of all the image data of the relevant patient after the image processing. For example, all the image data is transmitted to the PACS 2006, and data for accessing the image data transmitted to the PACS 2006 is sent to the diagnosis request management system 2009.

In the next step, step S5008, it is determined whether the transmission of the image data is completed. If the transmission is completed, the process flow advances to step S5002, and if the transmission is not yet completed, the determination in step S5008 is repeated.

A flow of processing executed by the diagnosis request management system 2009 is now described with reference to the flowchart of FIG. 30. First, in step S6001, the system 2009 determines whether there is radiographic image data for a patient for whom diagnosis is to be requested (this is done patient by patient). This determination is made based on information regarding radiographic image data in units of a patient, which is transmitted from the radiographing system 2003, another medical facility 2000', the diagnosis intermediating facility 4000, etc., e.g., on the above-mentioned information for accessing the image data transmitted to the PACS 2006. If the radiographic image data is present, the process flow advances to step S6002, and if it is not present, the process flow advances to step S6004.

In step S6002, the destination to which a diagnosis request for images of a diagnosis requested object is to be commissioned is decided, and information regarding the diagnosis request, including information of the diagnosis request destination, is registered in a storage for management of the progress of diagnosis. Here, the diagnosis request destination is decided based on information regarding the object images, e.g., information stored as header information of the object image data, etc., in the storage in association with the object images (such as the radiographed body part of the patient, the radiographing manner, the diagnosis purpose, the disease information, and information designated by the diagnosing doctor). The diagnosis request destination may be, as mentioned above, another medical facility 2000', the diagnosis intermediating facility 4000, etc. Then, in step S6003, the diagnosis request information including information for specifying the diagnosis object images or including data of the diagnosis object images is transmitted to the diagnosis request destination decided in the previous step, S6002.

Further, in step S6004, it is determined whether there is a new diagnosis report. This determination is made, for example, based on information received from the diagnosis terminal 2010, another medical facility 2000', the diagnosis intermediating facility 4000, etc. If the new diagnosis report is present, the process flow advances to step S6006, and if it is not present, the process flow advances to step S6005. In step S6005, it is determined whether there is an instruction to end the operation of the diagnosis request management system 2009. If the end of the operation is instructed, the diagnosis request management system 2009 brings the operation to an end. If the end of the operation is not instructed, the diagnosis request management system 2009 returns to step S6001 and continues the operation.

In step S6006, as a part of the diagnosis progress management, diagnosis report related information (such as the date of receipt and the contents of the report) is registered in the storage. Then, in step S6007, the diagnosis report is transmitted (transferred) to one or more predetermined transmission destinations among the computers, etc., in the HIS 2001, the RIS 2002, the PACS 2006, and a diagnosis requesting source (including another medical facility 2000', the diagnosis intermediating facility 4000, etc.). Thereafter, the diagnosis request management system 2009 advances to the determination process in the above step S6005.

Note that while the diagnosis request management system 2009 is constituted, by way of example, as a dedicated computer in the above-described embodiments, it is not limited such a configuration and may be functionally incorporated in, e.g., the HIS 2001, the RIS 2002, the radiography management/image processing server 2005 of the radiographing system 2003, or the PACS server 2007 of the PACS 2006.

As will be apparent from the above description, the present invention is able to achieve the object set forth above.

While the present invention has been described with reference to what are presently considered to be the preferred embodiments, the invention is not limited to the above embodiments and various changes and modifications can be made within the spirit and scope of the present invention. Therefore, to appraise the public of the scope of the present invention, the following claims are made.

What is claimed is:

1. A radiographic image processing method of processing a group of moving-state images of an object that were taken over a period of time and a still image of the same object, comprising:
   a first displaying step of displaying the group of moving-state images in turn and the still image;
   a region specifying step of specifying a region of interest in the still image;

a correlating step of correlating the region of interest in the still image with a region of interest in one image selected from the group of moving-state images;

a determining step of determining which region of the group of images the correlated region of interest of the still image corresponds to by calculating motion vectors between the group of all moving-state images;

a region specifying step of marking the respective positions corresponding to the region of interest in the group of moving-state images and the still image; and a second displaying step of displaying the marked group of moving-state images in turn.

2. A method according to claim 1, wherein said second displaying step further comprises a second displaying step of displaying the marked still image.

3. A method according to claim 1, wherein information identifying the region of interest is inputted in said region specifying step through a user interface.

4. A method according to claim 1, wherein the plurality of radiographs are displayed abreast of each other in said first image displaying step.

5. A radiographic image processing method of processing a group of moving-state images of an object that were over a period of time and a still image of the same object, comprising:

a region specifying step of specifying a region of interest in the still image;

a correlating step of correlating the region of interest in the still image with a region of interest in one image selected from the group of moving-state images;

a determining step of determining which region of the group of moving-state images the correlated region of interest of the still image corresponds to by calculating motion vectors between the group of all moving-state images;

a region specifying step of marking the respective positions corresponding to the region of interest in the group of moving-state images and the still image; and a displaying step of displaying the marked group of motive-state images in turn.

6. A radiographic image processing apparatus for processing a group of moving-state images of an object that were taken over a period of time and a still image of the same object, comprising:

a first displaying means for displaying the group of moving-state images in turn and the still image;

a region specifying means for specifying a region of interest in turn and the still images;

a correlating means for correlating the region of interest in the still image with a region of interest in one image selected from the group of moving-state images;

a determining means for determining which region of the group of moving-state images the correlated region of interest of the still image corresponds to by calculating motion vectors between the group of moving-state images;

a region specifying means for marking the respective positions corresponding to the region of all interest in the group of moving-state images and the still image; and a second displaying means for displaying the marked group of moving-state images in turn.

7. A program, stored in a computer-readable storage medium, in executable form, for causing a computer to execute a radiographic image processing method of processing a group of moving-state images of an object that were taken over a period of time and a still image of the same object, said method comprising:

a first displaying step of displaying the group of moving-state images in turn and the still image;

a region specifying step of specifying a region of interest in the still image;

a correlating step of correlating the region of interest in the still image with a region of interest in one image selected from the group of moving-state images;

a determining step of determining which region of the group of moving-state images the correlated region of interest of the still image corresponds to by calculating motion vectors between the group of all moving-state images;

a region specifying step of marking the respective positions corresponding to the region of interest in the group of moving-state images and the still image; and a second displaying step of displaying the marked group of moving-state images in turn.

8. A radiographic image processing method of processing a group of moving-state images of an object that were taken over a period of time and a still image of the same object, comprising:

a first displaying step of displaying the group of moving-state images in turn and the still image;

a region specifying step of specifying a region of interest in one of the group of moving-state images;

a determining step of determining which region of the group of moving-state images the specified region of interest of the still image corresponds to by calculating motion vectors between the group of all moving-state images;

a correlating step of correlating the region of interest in the one image selected from the group of moving-state images with a region of interest in the still image;

a region specifying step of marking the respective positions corresponding to the region of interest in the group of moving-state images and the still image; and a second displaying step of displaying the marked still image.

9. A radiographic image processing apparatus for processing a group of moving-state images of an object that were taken over a period of time and a still image of the same object, comprising:

a first displaying means for displaying the group of moving-state images in turn and the still image;

a region specifying means for specifying a region of interest in one of the group of moving-state images;

a determining means for determining which region of the group of moving-state images the specified region of all interest corresponds by calculating motion vectors between the group of all moving-state images;

a correlating means for correlating the region of interest in the one image selected from the group of moving-state images with a region of interest in the still image;

a region specifying means for marking the respective positions corresponding to the region of interest in the group of moving-state images and the still image; and a second displaying means for displaying the marked group of moving-state images in turn and displaying the marked still image.

10. A program for causing a computer to execute a radiographic image processing method of processing a group of moving-state images of an object that were taken with the lapse of time and a still image of the same object, said method comprising:

a first displaying step of displaying the group of moving-state images in turn and the still image;

a region specifying step of specifying a region of interest in one of the group of moving-state images;

a determining step of determining which region of the group of moving-state images the specified region of interest of the still image corresponds to by calculating motion vectors between the group of all moving-state images;

a correlating step of correlating the region of interest in the one image selected from the group of moving-state images with a region of interest in the still image;

a region specifying step of marking the respective positions corresponding to the region of interest in the group of moving-state images and the still image; and a second displaying step of displaying the marked group of moving-state images in turn and displaying the marked still image.

* * * * *

UNITED STATES PATENT AND TRADEMARK OFFICE
CERTIFICATE OF CORRECTION

PATENT NO.        : 7,158,661 B2
APPLICATION NO. : 10/291580
DATED             : January 2, 2007
INVENTOR(S)      : Hitoshi Inoue It is certified that error appears in the above-identified patent and that said Letters Patent is hereby corrected as shown below:

COLUMN 1

Line 59, "amount" should read --number--.

COLUMN 14

Line 1, "diagnosis" should read --diagnoses--.

COLUMN 21

Line 23, "were" should read --were taken--.

COLUMN 22

Line 52, "corresponds" should read --corresponds to--.

Signed and Sealed this

Fifteenth Day of April, 2008

JON W. DUDAS
*Director of the United States Patent and Trademark Office*